United States Patent
Satomaa et al.

(10) Patent No.: US 11,793,886 B2
(45) Date of Patent: Oct. 24, 2023

(54) HYDROPHILIC LINKERS AND CONJUGATES THEREOF

(71) Applicant: GLYKOS FINLAND OY, Helsinki (FI)

(72) Inventors: Tero Satomaa, Helsinki (FI); Jari Helin, Rajamäki (FI); Juhani Saarinen, Helsinki (FI)

(73) Assignee: Glykos Finland Oy, Helsinki (FI)

( * ) Notice: Subject to any disclaimer, the term of this patent is extended or adjusted under 35 U.S.C. 154(b) by 627 days.

(21) Appl. No.: 16/623,226

(22) PCT Filed: Jun. 20, 2018

(86) PCT No.: PCT/FI2018/050483
§ 371 (c)(1),
(2) Date: Dec. 16, 2019

(87) PCT Pub. No.: WO2018/234636
PCT Pub. Date: Dec. 27, 2018

(65) Prior Publication Data
US 2020/0323995 A1    Oct. 15, 2020

(30) Foreign Application Priority Data

| Jun. 21, 2017 | (FI) | 20177078 |
| Jun. 22, 2017 | (FI) | 20177079 |
| Sep. 19, 2017 | (FI) | 20177107 |
| Sep. 20, 2017 | (FI) | 20177108 |

(51) Int. Cl.
| A61K 47/68 | (2017.01) |
| A61K 47/65 | (2017.01) |
| A61K 47/54 | (2017.01) |
| A61P 35/00 | (2006.01) |

(52) U.S. Cl.
CPC ........ *A61K 47/6855* (2017.08); *A61K 47/549* (2017.08); *A61K 47/65* (2017.08); *A61K 47/6803* (2017.08); *A61P 35/00* (2018.01)

(58) Field of Classification Search
CPC . A61K 47/65; A61K 47/6803; A61K 47/6809
See application file for complete search history.

(56) References Cited

U.S. PATENT DOCUMENTS

| 2004/0018974 A1 | 1/2004 | Abrogast et al. |
| 2005/0096263 A1 | 5/2005 | Keay et al. |
| 2005/0147555 A1 | 7/2005 | Fan et al. |
| 2005/0222398 A1 | 10/2005 | Danishefsky et al. |
| 2012/0101043 A1 | 4/2012 | Polt et al. |
| 2014/0170704 A1 | 6/2014 | Young et al. |
| 2014/0014851 A1 | 10/2014 | Nguyen |
| 2014/0294851 A1 | 10/2014 | Nguyen |

FOREIGN PATENT DOCUMENTS

| DE | 10305607 A1 | 3/2004 | |
| EP | 2050761 A1 | 4/2009 | |
| WO | 2000052046 A1 | 9/2000 | |
| WO | 2004017810 A2 | 3/2004 | |
| WO | 2004022590 A2 | 3/2004 | |
| WO | 2008040362 A2 | 4/2008 | |
| WO | 2009108807 A1 | 9/2009 | |
| WO | 2013087993 A1 | 6/2013 | |
| WO | 2014088432 A1 | 6/2014 | |
| WO | 2014096551 A1 | 6/2014 | |
| WO | WO2014088432 * | 6/2014 | ............. C07H 15/04 |
| WO | 2014177771 A1 | 11/2014 | |
| WO | 2015189477 A1 | 12/2015 | |
| WO | 2015189478 A1 | 12/2015 | |
| WO | 2016001485 A1 | 1/2016 | |

OTHER PUBLICATIONS

Burke, P. J. et al., Optimization of a PEGylated glucuronide-monomethylauristatin E linker for antibody-drug conjugates, Mol Cancer Ther, 2017, vol. 16, No. 1, pp. 116-123.

Rangappa, S. et al., Effects of the multiple O-glycosylation states on antibody recognition of the immunodomminantmotif in MUC1 extracellular tandem repeats, Med. Chem. Commun., 2016, vol. 7, pp. 1102-1122.

St. Hilaire, P. M. et al., Oligosaccharide mimetics obtained by novel, rapid screening of carboxylic acid encoded glycopeptide libraries, J. Am. Chem. Soc., 1998, vol. 120, pp. 13312-1332.

Chen, J et al., Development of a native nanoelectrospray mass spectrometry method for determination of the drug-to-antibody ratio of antibody-drug conjugates. Anal Chem. 2013;85(3):1699-704. https://pubs.acs.org/doi/pdf/10.1021/ac302959p.

Ekholm, FS et al., Introducing Glycolinkers for the Functionalization of Cytotoxic Drugs and Applications in Antibody-Drug Conjugation Chemistry. ChemMedChem. 2016;11(22):2501-2505.

(Continued)

*Primary Examiner* — Pancham Bakshi
(74) *Attorney, Agent, or Firm* — Patrick J. Halloran

(57) ABSTRACT

Hydrophilic linkers and their conjugates are disclosed. Formula (I) (II)

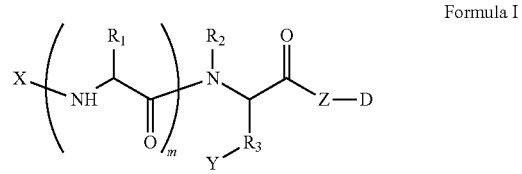

Formula I

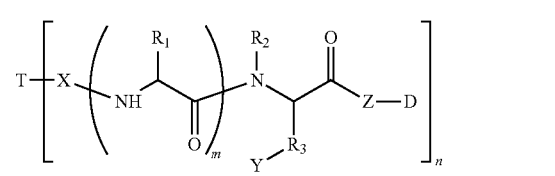

Formula II

28 Claims, 6 Drawing Sheets

(56) References Cited

OTHER PUBLICATIONS

Ekholm, FS et al., Synthesis of the copper chelator TGTA and evaluation of its ability to protect biomolecules from copper induced degradation during copper catalyzed azide-alkyne bioconjugation reactions. Org Biomol Chem. 2016l;14(3):849-52.
Liu, X et al., Structurally defined synthetic cancer vaccines: analysis of structure, glycosylation and recognition of cancer associated mucin, MUC-1 derived peptides. Glycoconj J. 1995;12(5):607-17.
Miller, ML et al., A New Class of Antibody-Drug Conjugates with Potent DNA Alkylating Activity. Mol Cancer Ther. 2016;15(8):1870-8.
Rangappa, et al., Effects of the multiple O-glycosylation states on antibody recognition of the immunodominant motif in MUC1 extracellular tandem repeats. Med Chem Comm 2016;7(6):1102-1122.
Satomaa, T, et al., Hydrophilic Auristatin Glycoside Payload Enables Improved Antibody-Drug Conjugate Efficacy and Biocompatibility. Antibodies (Basel). 2018;7(2).
Tavernaro, I et al., Synthesis of tumor-associated MUC1-glycopeptides and their multivalent presentation by functionalized gold colloids. Org Biomol Chem. 2015;13(1):81-97.
Yates, LM, et al., A Stable Pyrophosphoserine Analog for Incorporation into Peptides and Proteins. ACS Chem Biol. 2016;11(4):1066-73. https://pubs.acs.org/doi/10.1021/acschembio.5b00972.
PCT/FI2018/050483 International Search Report (dated Sep. 18, 2018).

* cited by examiner

HYDROPHILIC LINKERS AND CONJUGATES THEREOF

This application was filed under 35 U.S.C. § 371 and claims priority to International Application No. PCT/FI2018/050483 filed June 20, 2018, and claims priority to FI 20177108 filed filed Sep. 20, 2017, FI 20177107 filed filed Sep. 19, 2017, FI 20177079 filed filed June 22, 2017, and FI 20177078 filed filed Jun. 21, 2017, which are hereby incorporated by reference into this disclosure in their entirety.

FIELD OF THE INVENTION

The invention relates to a linker, a linker-payload conjugate, a targeting unit-linker-payload conjugate, methods for preparing the same, a pharmaceutical composition and a method of treating and/or modulating the growth of and/or prophylaxis of tumor cells.

SUMMARY

The linker-payload conjugate is characterized by what is presented in claim 1.

The targeting unit-linker-payload conjugate is characterized by what is presented in claim 3.

The method for preparing the targeting unit-linker-payload conjugate is characterized by what is presented in claim 21.

The pharmaceutical composition is characterized by what is presented in claim 22.

The pharmaceutical composition for use as a medicament or use in the treatment of cancer is characterized by what is presented in claim 23.

The method of treating and/or modulating the growth of and/or prophylaxis of tumor cells in humans or animals is characterized by what is presented in claim 24.

FIGURE LEGENDS

Figure 1:
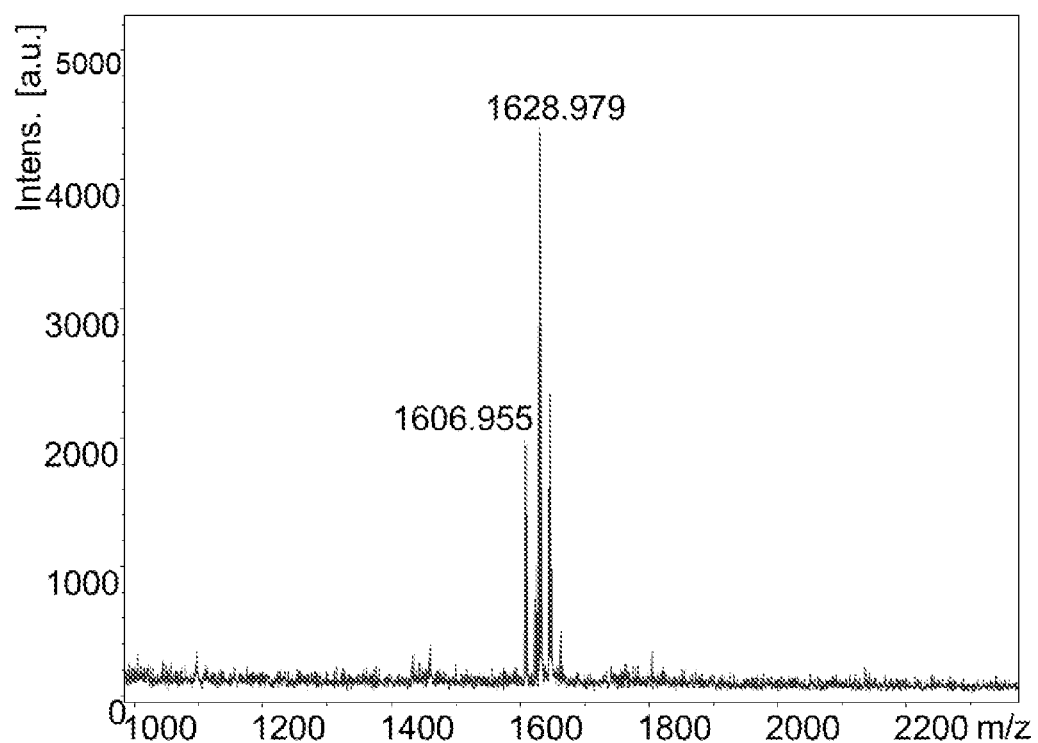

FIG. 1 shows matrix-assisted laser desorption-ionization time-of-flight (MALDI-TOF) mass spectrometric analysis of maleimidocaproyl-Val-Ser(Glc)-PAB-MMAU. Observed signals at m/z 1606.955 for the [M+Na]$^+$ ion and at m/z 1628.979 for the [M−H+2Na]$^+$ ion demonstrate successful preparation of the linker-drug conjugate.

Figure 2:
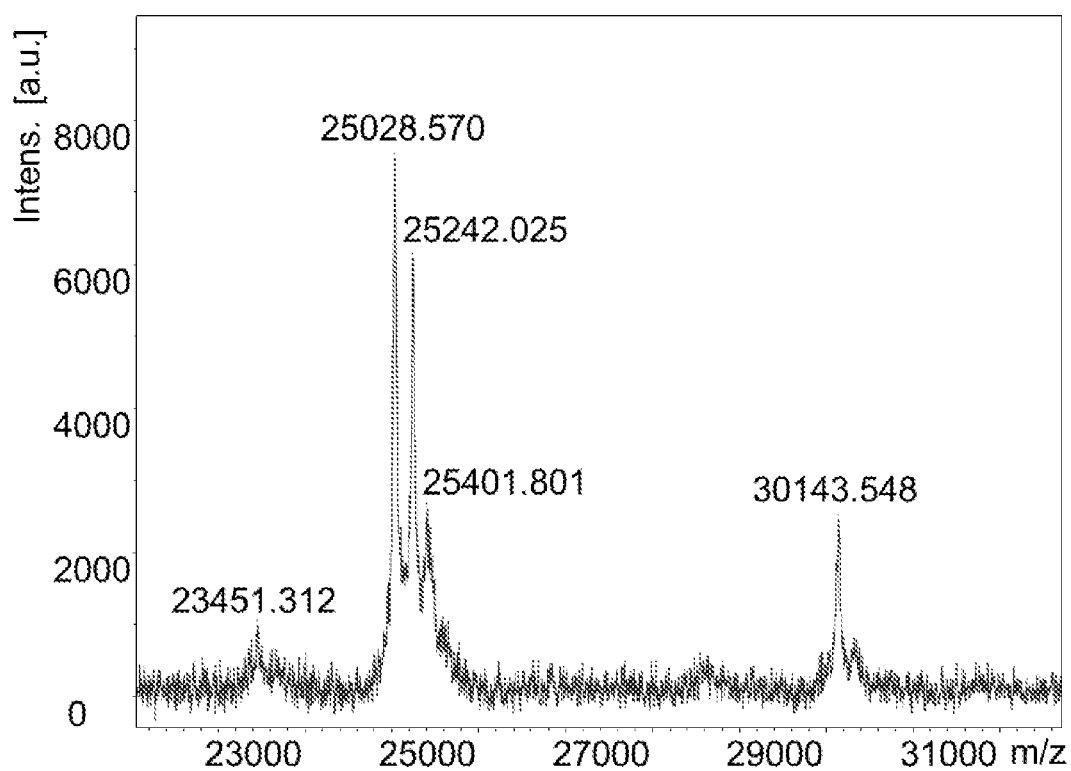

FIG. 2 shows MALDI-TOF mass spectrometric analysis of successfully prepared trastuzumab-maleimidocaproyl-Val-Ser(Glc)-PAB-MMAU conjugate with drug-to-antibody (DAR) ratio of about 8 (DAR=8). Observed signals: light chain at m/z 23451.312; light chain+1 linker-drug conjugate at m/z 25028.570; Fabricator enzyme-cleaved heavy chain Fc fragment at m/z 25242.025, corresponding to fragment cleaved after PAPELLG sequence with FG0 glycan and without C-terminal lysine, and at m/z 25401.801, corresponding to fragment with FG1 glycan and without C-terminal lysine; Fabricator enzyme-cleaved heavy chain Fc fragment at m/z 30143.548, corresponding to fragment with three linker-MMAU conjugates.

Figure 3:
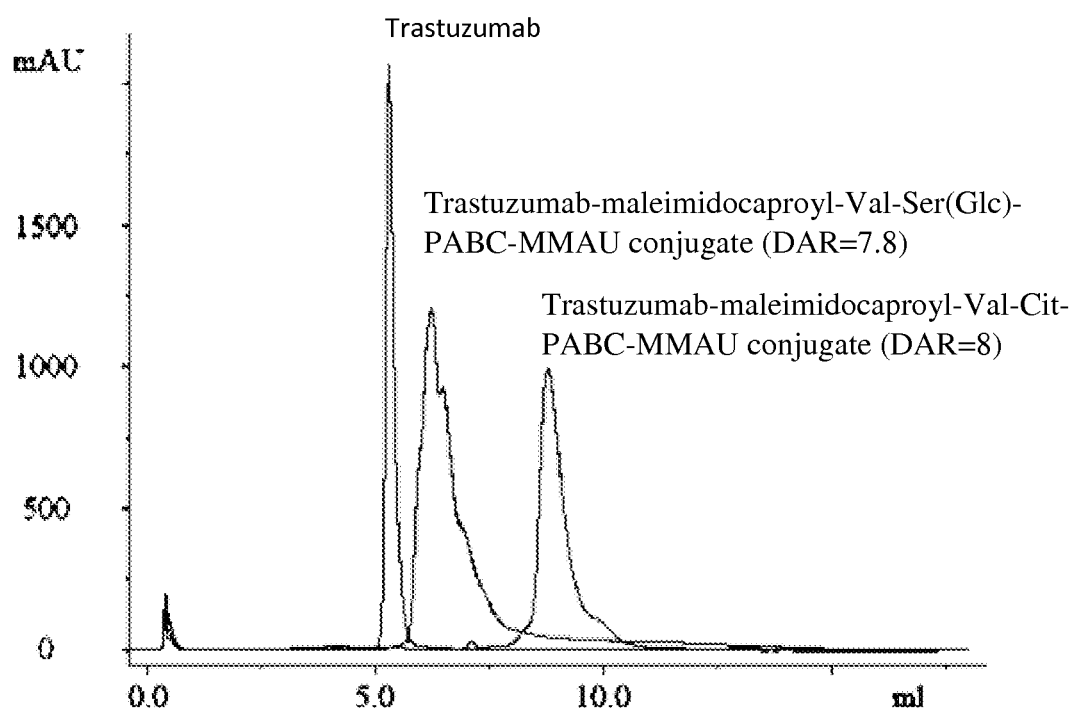

FIG. 3 shows overlaid HIC HPLC chromatograms of the naked antibody trastuzumab, DAR=7.8 trastuzumab-maleimidocaproyl-Val-Ser(Glc)-PABC-MMAU conjugate and DAR=8 maleimidocaproyl-Val-Cit-PAB-MMAU conjugate prepared using standard Val-Cit linker. The elution position of trastuzumab-maleimidocaproyl-Val-Ser(Glc)-PABC-MMAU (DAR=7.8) was at 6.2 ml (comparable to trastuzumab at 5.3 ml), showing markedly more hydrophilicity than maleimidocaproyl-Val-Cit-PABC-MMAU (DAR=8) eluting at 8.8 ml.

Figure 4:
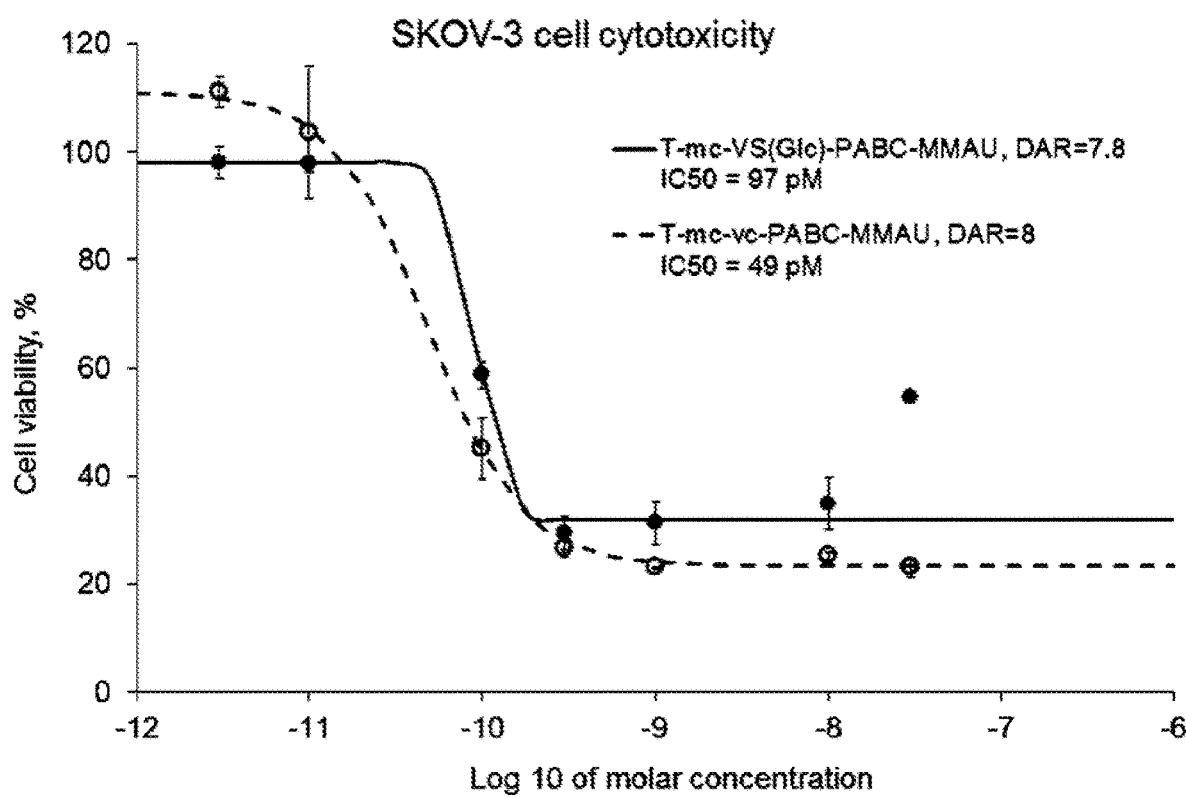

FIG. 4 shows cytotoxicity to HER2+ SKOV-3 ovarian cancer cells of serial dilutions of trastuzumab-maleimidocaproyl-Val-Ser(Glc)-PABC-MMAU conjugate (DAR=7.8; solid line and solid circles) and trastuzumab-maleimidocaproyl-Val-Cit-PABC-MMAU conjugate (DAR=8; dashed line and open circles). Both ADCs had cytotoxicity with IC50 below 100 pM, showing that the trastuzumab-maleimidocaproyl-Val-Ser(Glc)-PABC-MMAU conjugate was highly active as an ADC and that the linker was effectively cleaved inside the cancer cells.

Figure 5:
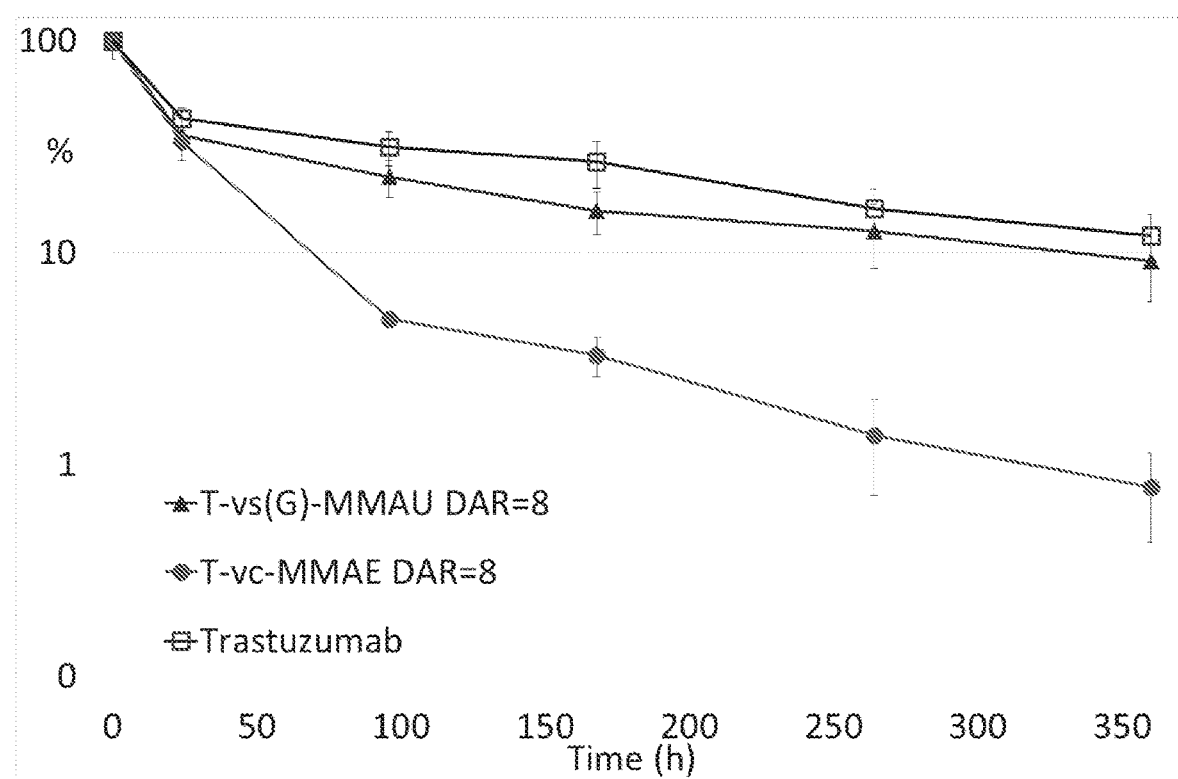

FIG. 5 shows pharmacokinetics of the conjugates in mice. Groups of four mice were given 10 mg/kg single dose i.v. injection of either trastuzumab (Roche; open squares), trastuzumab-maleimidocaproyl-Val-Cit-PABC-MMAE conjugate (DAR=8; solid circles) or trastuzumab-maleimidocaproyl-Val-Ser(Glc)-PABC-MMAU conjugate (DAR=8; solid triangles). Amount of the substances were measured by ELISA assay at indicated time points. y-axis shows the relative amount of each test substance compared to their initial value at 5 minutes after the injection (% of original).

Figure 6:
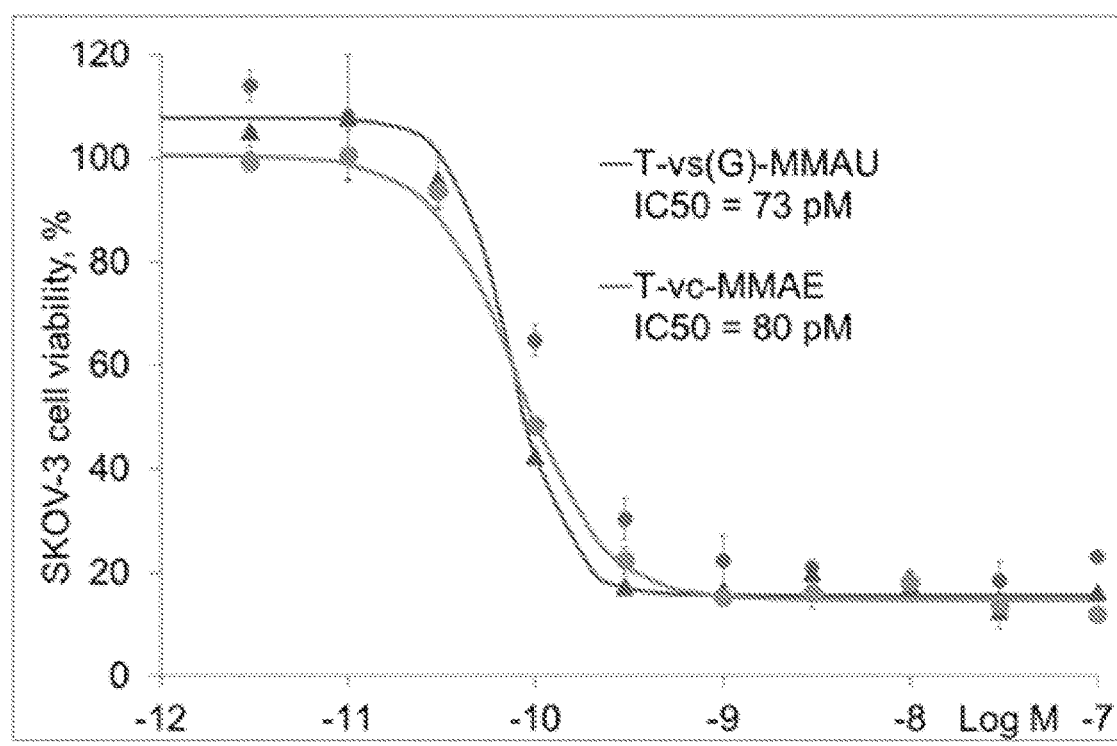

FIG. 6 shows that efficacy of the Val-Ser(Glc) linker cleavage was comparable to Val-Cit linker cleavage after internalization of ADC into target cells, as demonstrated by cytotoxicity assay in SKOV-3 ovarian cancer cells.

DETAILED DESCRIPTION

The present invention provides linkers that are conjugated to a payload molecule. In an embodiment, the present invention provides cleavable hydrophilic linkers comprising a cleavable hydrophilic group.

The presence of a cleavable hydrophilic group in the linker may provide several benefits, such as i) higher water solubility of the final product, ii) higher resistance towards aggregation in aqueous solutions, iii) ability to link a higher number of payload molecules per molecule of cell binder, iv) higher in vivo stability, and therefore, both v) improved efficacy towards the target and vi) improved safety to non-target cells and tissues.

In an embodiment of the present invention, the presence of a cleavable hydrophilic group in the linker may prevent premature cleavage of the linker before the conjugate reaches its target, which further contributes to the benefits named above.

In an embodiment, the presence of a hydrophilic group in the linker improves the pharmacokinetics of the conjugate improving its in vivo exposure, which may further contribute to the benefits named above.

In this context, the term "linker" should be understood as referring to the moiety or portion of a molecule represented by Formulas I and II that does not comprise D and T and m is 0, or as referring to the moiety or portion of a molecule represented by Formulas I and II that does not comprise D and T and m is 1.

The present invention provides a linker-payload conjugate of Formula I

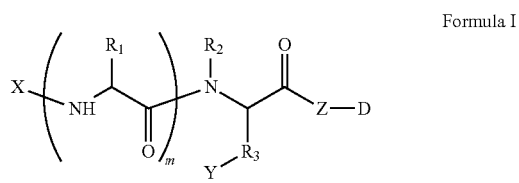

Formula I wherein X is either absent or a spacer group; $R_1$ is an amino acid side chain; $R_2$ is H, an alkyl group, an aryl group, or a halide; Y is a hydrophilic group; $R_3$ is an amino acid side chain; Z is either absent or a self-immolative group; D is a payload molecule; and m is either 0 or 1.

The present invention further provides a targeting unit-linker-payload conjugate of Formula II

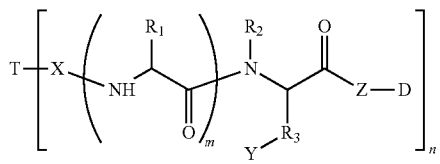

Formula II wherein T is a targeting unit; X is either absent or a spacer group; $R_1$ is an amino acid side chain; $R_2$ is H, an alkyl group, an aryl group, or a halide; Y is a hydrophilic group; $R_3$ is an amino acid side chain; Z is either absent or a self-immolative group; D is a payload molecule; m is either 0 or 1; and n is an integer >1.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4.

In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, n is 5.

In an embodiment, n is 6.

In an embodiment, n is 7.

In an embodiment, n is 8.

In an embodiment, n is 9.

The present invention further provides a targeting unit-linker-payload conjugate of Formula III

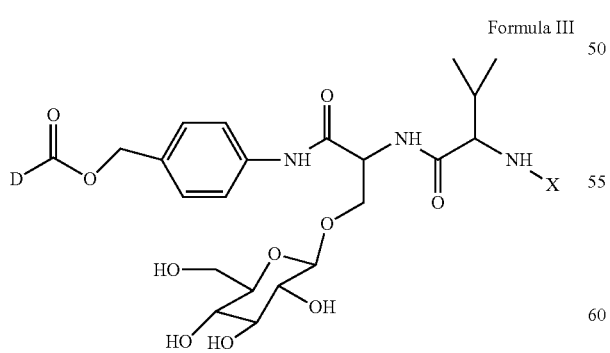

Formula III wherein X is a spacer group comprising a maleimide and D is a payload molecule.

The present invention further provides linker-payload conjugates of Formula IIIb, Formula IIIc and Formula IIId:

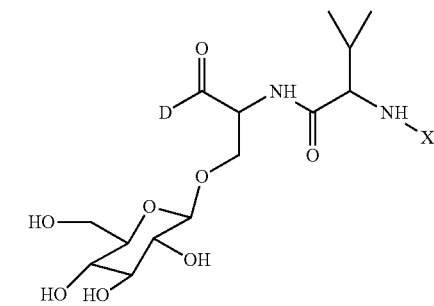

Formula IIIb

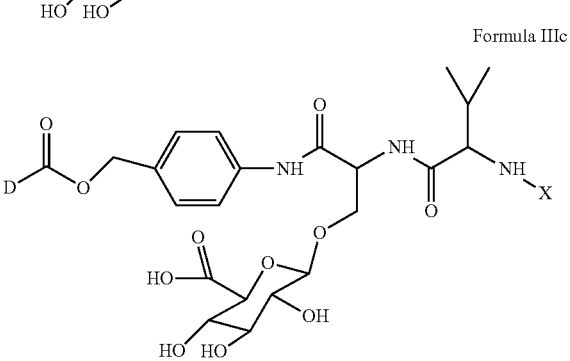

Formula IIIc

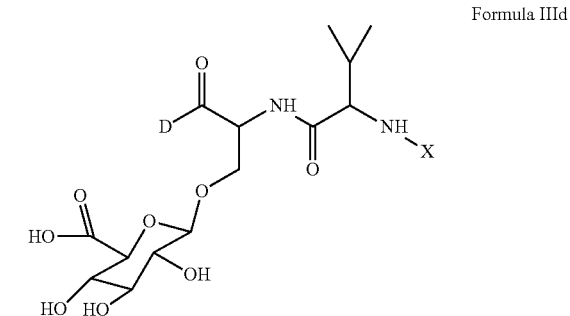

Formula IIId wherein X is a spacer group comprising a maleimide or an azide-reactive group and D is a payload molecule.

The present invention further provides a targeting unit-linker-payload conjugate of Formula IV

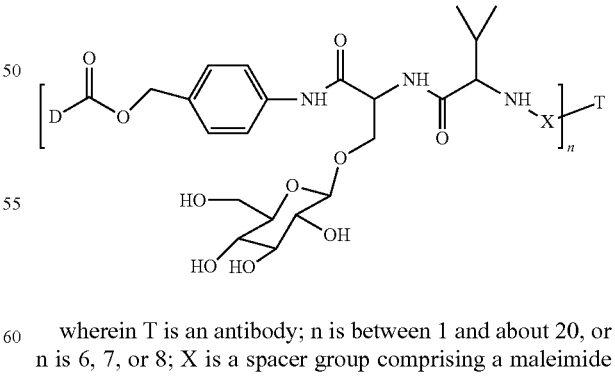

Formula IV wherein T is an antibody; n is between 1 and about 20, or n is 6, 7, or 8; X is a spacer group comprising a maleimide connected to a cysteine side chain of the antibody via a thioether bond; and D is a payload molecule.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4.

In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, n is 5.
In an embodiment, n is 6.
In an embodiment, n is 7.
In an embodiment, n is 8.
In an embodiment, n is 9.

The present invention further provides targeting unit-linker-payload conjugates of Formula IVb, Formula IVc and Formula IVd:

Formula IVb

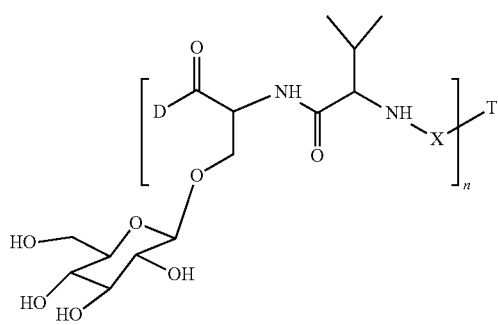

Formula IVc

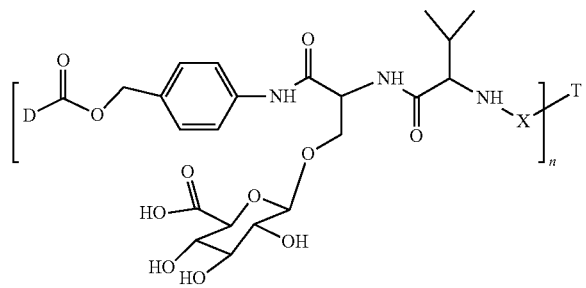

Formula IVd

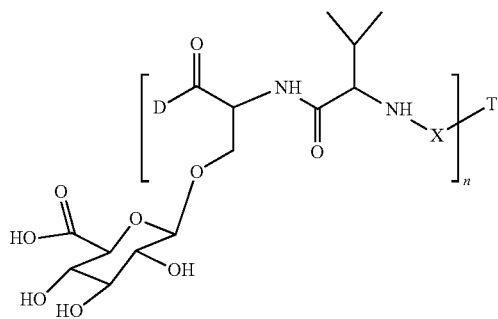

wherein T is an antibody; n is between 1 and about 20, or n is 6, 7, or 8, or n is 2 or 4; X is a spacer group comprising a maleimide connected to a cysteine side chain of the antibody via a thioether bond, or X is a spacer group comprising a azide-reactive group connected to a azide group in the antibody via a 1,3-triazole; and D is a payload molecule.

The present invention further provides a linker-payload conjugate of Formula V.

A skilled person will recognize that the linker-payload conjugate moiety linked to targeting unit or spacer as represented in Formula II is essentially the same as represented by Formula I. In the targeting unit-linker-payload conjugate, the targeting unit, T, and the payload, D, have thus reacted at the two ends of the linker (without X and/or Y), or reacted with the X and/or Y of the linker. Using the linkers according to the invention, one or more payload molecules can be introduced to a targeting unit. Using the hydrophilic linkers according to the invention comprising the hydrophilic group Y, a higher number of payload molecules can be introduced.

In an embodiment, the linker-payload conjugate may be represented as of Formula T-X-L-Z-D, wherein T, X, Z, and D are as represented in Formulas I and II and L is the linker of the present invention.

In an embodiment, Y is selected from the group consisting of a saccharide, phosphate ester, sulfate ester, a phosphodiester and a phosphonate.

In an embodiment, Y is a saccharide.

The term "saccharide" should be understood as referring to single simple sugar moieties or monosaccharides or their derivatives, as well as combinations of two or more single sugar moieties or monosaccharides covalently linked to form disaccharides, oligosaccharides, and polysaccharides.

The term "monosaccharide" should be understood to include trioses, tetroses, pentoses, hexoses, heptoses, octoses or nonoses. One or several of the hydroxyl groups in the chemical structure can be replaced with other groups such as hydrogen, amino, amine, acylamido, acetylamido, halogen, mercapto, acyl, acetyl, phosphate or sulphate ester, and the like; and the saccharides can also comprise other functional groups such as carboxyl, carbonyl, hemiacetal, acetal and thio groups. A monosaccharide can selected from the group including, but not limited to, simple aldoses such as glyceraldehyde, erythrose, threose, ribose, arabinose, xylose, lyxose, allose, altrose, glucose, mannose, gulose, idose, galactose, talose and mannoheptulose; simple ketoses such as dihydroxyacetone, erythrulose, ribulose, xylulose, psicose, fructose, sorbose, tagatose and sedoheptulose; deoxysugars such as fucose, 2-deoxyglucose, 2-deoxyribose and rhamnose; sialic acids such as ketodeoxynonulosonic acid, N-acetylneuraminic acid and 9-O-acetyl-N-acetylneuraminic acid; uronic acids such as glucuronic acid, galacturonic acid and iduronic acid; amino sugars such as 2-amino-2-deoxygalactose and 2-amino-2-deoxyglucose; acylamino sugars such as 2-acetamido-2-deoxygalactose, 2-acetamido-2-deoxyglucose and N-glycolylneuraminic acid; phosphorylated and sulphated sugars such as 6-phosphomannose, 6-sulpho-N-acetylglucosamine and 3-sulphogalactose; and derivatives and modifications thereof. The monosaccharide can also be a non-reducing carbohydrate such as inositol or alditol or their derivative.

Saccharides and monosaccharides according to the present invention may be in D- or L-configuration; in open-chain, pyranose or furanose form; α or β anomer; and any combination thereof.

The term "oligosaccharide" should be understood as referring to saccharides composed of two or several monosaccharides linked together by glycosidic bonds having a degree of polymerization in the range of from 2 to about 20. The term "oligosaccharide" should be understood as referring to hetero- and homopolymers that can be either branched, linear or cyclical.

In an embodiment, the oligosaccharide has a reducing end and a non-reducing end, whether or not the saccharide at the reducing end is in fact a reducing sugar.

The term "disaccharide" should be understood as referring to an oligosaccharide composed of two monosaccharides linked together by a glycosidic bond. Examples of disaccharides include, but are not limited to, lactose, N-acetyllactosamine, galactobiose, maltose, isomaltose and cellobiose.

The term "trisaccharide" should be understood as referring to a saccharide composed of three monosaccharides linked together by glycosidic bonds. Examples of trisaccharides include, but are not limited to, maltotriose, sialyllactose, globotriose, lacto-N-triose and gangliotriose. In an embodiment, the saccharide is a monosaccharide, a disaccharide, a trisaccharide or an oligosaccharide.

In an embodiment, the saccharide comprises β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid or any analogue or modification thereof.

In an embodiment, the saccharide consists of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid or any analogue or modification thereof.

In an embodiment, the saccharide consists of β-D-glucose, N-acetyl-β-D-glucosamine, β-D-glucuronic acid or α-L-fucose.

In an embodiment, the saccharide comprises β-D-glucose.

In an embodiment, the saccharide consists of β-D-glucose.

In an embodiment, the modification is sulfate, phosphate, carboxyl, amino, or O-acetyl modification of the monosaccharide.

The term "analogue" or "being analogous to" should be understood so that the analogue or the analogous monosaccharide is cleavable by the same enzyme than the monosaccharide to which it is analogous to.

The term "modification" or "modification of a monosaccharide" should be understood so that the modification is a covalent modification of a monosaccharide resulting from substitution of a functional group or an atom of the monosaccharide.

In an embodiment, the modification is selected from the group of sulfate, phosphate, carboxyl, amino, and O-acetyl modification.

In an embodiment, Y is cleavable by an enzyme.

In an embodiment, Y is cleavable by an enzyme, for example, an intracellular enzyme, a lysosomal enzyme or a cytoplasmic enzyme.

In an embodiment, the cleavable hydrophilic group Y is a saccharide and cleavable by an enzyme.

In an embodiment, the saccharide is β-D-glucose, N-acetyl-β-D-glucosamine, β-D-glucuronic acid or α-L-fucose.

In an embodiment, the saccharide is β-D-glucose.

In an embodiment, the enzyme is an intracellular enzyme, a lysosomal enzyme or a cytoplasmic enzyme.

In an embodiment, the intracellular enzyme is a glucosidase, a hexosaminidase, an N-acetylglucosaminidase, a glucuronidase or a fucosidase.

In an embodiment, the lysosomal enzyme is a glucosidase, a hexosaminidase, an N-acetylglucosaminidase, a glucuronidase or a fucosidase.

In an embodiment, the lysosomal enzyme is β-glucosidase.

In an embodiment, the cytoplasmic enzyme is a glucosidase, a hexosaminidase, an N-acetylglucosaminidase, a glucuronidase or a fucosidase.

In an embodiment, the saccharide such as β-D-glucose is cleavable by a lysosomal or an intracellular enzyme. This embodiment has the utility that lysosomal or intracellular enzymes may remove the saccharide inside a cell. A skilled person is capable of selecting a saccharide that is cleavable by a lysosomal or an intracellular enzyme based on biochemical literature; various such enzymes having different specificities are known.

In an embodiment, the lysosomal or intracellular enzyme is capable of removing the entire saccharide inside a cell.

In an embodiment, one or more of the glycosidic bonds of the saccharide are essentially stable in neutral pH and/or in serum.

In an embodiment, all glycosidic bonds of the saccharide are essentially stable in neutral pH and/or in serum.

In an embodiment, one or more of the glycosidic bonds of the saccharide are cleavable in tumor microenvironment outside a cell. This embodiment has the added utility that the saccharide may be removed more efficiently inside a tumor than in normal tissue and the molecule may be more efficiently taken up by cancer cells than by normal cells.

In an embodiment, the saccharide protects the linker from cleavage by a peptidase before the saccharide is cleaved by a glycosidase enzyme.

In an embodiment, the saccharide is β-D-glucose that protects the linker from cleavage by a peptidase before the saccharide is cleaved by β-glucosidase.

In an embodiment, the saccharide protects the linker from cleavage by cathepsin before the saccharide is cleaved by a glycosidase enzyme.

In an embodiment, the saccharide is β-D-glucose that protects the linker from cleavage by cathepsin before the saccharide is cleaved by β-glucosidase.

In an embodiment, the lysosomal or intracellular enzyme is selected from the group consisting of β-galactosidase, β-hexosaminidase, α-N-acetylgalactosaminidase, β-N-acetylglucosaminidase, β-glucuronidase, α-L-iduronidase, α-galactosidase, α-glucosidase, β-glucosidase, α-mannosidase, β-mannosidase, α-fucosidase, β-xylosidase and neuraminidase. In an embodiment, the human glycohydrolase is selected from the group consisting of β-galactosidase, β-hexosaminidase, α-N-acetylgalactosaminidase, β-N-acetylglucosaminidase, β-glucuronidase, α-L-iduronidase, α-galactosidase, α-glucosidase, β-glucosidase, α-mannosidase, β-mannosidase, α-fucosidase, β-xylosidase and neuraminidase.

In an embodiment, Y is phosphate ester.

In an embodiment, Y is sulfate ester.

In an embodiment, Y is a phosphodiester.

In an embodiment, the phosphodiester is pyrophosphate, O—P(=O)(OH)—O—P(=O)(OH)$_2$.

In an embodiment, the phosphodiester is a substituted pyrophosphate selected from the group of O—P(=O)(OH)—O—P(=O)(OH)OR and O—P(=O)(OH)—O—P(=O)(OH)R, wherein R is selected from the group of P(=O)(OH)R, CH$_3$, an alkyl group and an aryl group. In an embodiment, the alkyl group is CH$_2$CH$_2$NH$_2$. In an embodiment, the aryl group is benzyl.

In an embodiment, Y is a phosphonate.

In an embodiment, the phosphonate is bisphosphonate, O—P(=O)(OH)—CH$_2$—P(=O)(OH)$_2$.

In an embodiment, the phosphonate is substituted bisphosphonate selected from the group of O—P(=O)(OH)—CH$_2$—P(=O)(OH)OR and O—P(=O)(OH)—CH$_2$—P(=O)(OH)R, wherein R is selected from the group of P(=O)(OH)R, CH$_3$, an alkyl group and an aryl group. In an embodiment, the alkyl group is $CH_2CH_2NH_2$. In an embodiment, the aryl group is benzyl.

Phosphodiester and bisphosphonate groups according to the invention can be prepared as described in Yates and Fiedler, ACS Chem. Biol. 2016, 11, 1066-1073, and incorporated as protected modified amino acids such as protected phosphodiester-modified or protected bisphosphonate-modified serine building blocks in standard peptide synthesis chemistry to produce the linker moieties according to the present invention.

In an embodiment, the cleavable hydrophilic group Y inhibits an endopeptidase from liberating the payload D from the conjugate until Y is first cleaved away from the conjugate.

In an embodiment, $R_3$ is a side chain of an amino acid.

In an embodiment, $R_3$ is the side chain of an α-amino acid, serine, threonine or tyrosine.

In an embodiment, $R_3$ is the side chain of serine.

As used herein, "amino acid side chain" refers the monovalent hydrogen or non-hydrogen substituent bonded to the α-carbon of an α-amino acid, including α-amino acid and non-α-amino acids. Exemplary amino acid side chains include, but are not limited to, the α-carbon substituent of glycine, alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, and citrulline.

An amino acid according to the present invention may be in L- or D-configuration; in free amino acid or amino acid residue form; and any combination thereof.

In an embodiment, $R_2$ is H, $CH_3$, an alkyl group, an aryl group, or a halide.

In an embodiment, $R_2$ is H.

In an embodiment, $R_2$ is $CH_3$.

In an embodiment, $R_2$ is a halide.

In an embodiment, the halide is F, Cl or I.

In an embodiment, $R_2$ is an alkyl group.

The term "alkyl" should be understood as referring to a straight or branched chain saturated or unsaturated hydrocarbon having the indicated number of carbon atoms (e.g., "$C_1$-$C_8$ alkyl" refers to an alkyl group having from 1 to 8 carbon atoms). When the number of carbon atoms is not indicated, the alkyl group has from 1 to 8 carbon atoms. Representative "$C_1$-$C_8$ alkyl" groups include (but are not limited to) methyl (Me, $CH_3$), ethyl (Et, $CH_2CH_3$), 1-propyl (n-Pr, n-propyl, $CH_2CH_2CH_3$), 2-propyl (i-Pr, isopropyl, $CH(CH_3)_2$), 1-butyl (n-Bu, n-butyl, $CH_2CH_2CH_2CH_3$), 2-methyl-1-propyl (i-Bu, isobutyl, $CH_2CH(CH_3)_2$), 2-butyl (s-Bu, s-butyl, $CH(CH_3)CH_2CH_3$), 2-methyl-2-propyl (t-Bu, tert-butyl, $C(CH_3)_3$), 1-pentyl (n-pentyl, $CH_2CH_2CH_2CH_2CH_3$), 2-pentyl ($CH(CH_3)CH_2CH_2CH_3$), 3-pentyl ($CH(CH_2CH_3)_2$), 2-methyl-2-butyl ($C(CH_3)_2CH_2CH_3$), 3-methyl-2-butyl ($CH(CH_3)CH(CH_3)_2$), 3-methyl-1-butyl ($CH_2CH_2CH(CH_3)_2$), 2-methyl-1-butyl ($CH_2CH(CH_3)CH_2CH_3$), 1-hexyl ($CH_2CH_2CH_2CH_2CH_2CH_3$), 2-hexyl ($CH(CH_3)CH_2CH_2CH_2CH_3$), 3-hexyl ($CH(CH_2CH_3)(CH_2CH_2CH_3)$), 2-methyl-2-pentyl ($C(CH_3)_2CH_2CH_2CH_3$), 3-methyl-2-pentyl ($CH(CH_3)CH(CH_3)CH_2CH_3$), 4-methyl-2-pentyl ($CH(CH_3)CH_2CH(CH_3)_2$), 3-methyl-3-pentyl ($C(CH_3)(CH_2CH_3)_2$), 2-methyl-3-pentyl ($CH(CH_2CH_3)CH(CH_3)_2$), 2,3-dimethyl-2-butyl ($C(CH_3)_2CH(CH_3)_2$), and 3,3-dimethyl-2-butyl ($CH(CH_3)C(CH_3)_3$). An alkyl group can be unsubstituted or substituted with one or more groups including, but not limited to, OH, $O(C_1$-$C_8$ alkyl), aryl, COR', OCOR', $CONH_2$, CONHR', $CONR'_2$, NHCOR', SH, $SO_2R'$, SOR', $OSO_2OH$, $OPO(OH)_2$, halogen, $N_3$, $NH_2$, NHR', $NR'_2$, $NHCO(C_1$-$C_8$ alkyl) or CN, wherein each R' is independently either H, $C_1$-$C_8$ alkyl or aryl. The term "alkyl" should also be understood as referring to an alkylene, a saturated, branched or straight chain or cyclic hydrocarbon radical of 1-18 carbon atoms, and having two monovalent radical centers derived by the removal of two hydrogen atoms from the same or two different carbon atoms of a parent alkane. Typical such alkylenes include (but are not limited to) methylene ($CH_2$) 1,2-ethyl ($CH_2CH_2$), 1,3-propyl ($CH_2CH_2CH_2$), 1,4-butyl ($CH_2CH_2CH_2CH_2$), and the like. The term "alkyl" should also be understood as referring to arylalkyl and heteroarylalkyl radicals as described below.

The term "arylalkyl" should be understood as referring to an acyclic alkyl radical in which one of the hydrogen atoms bonded to a carbon atom, typically a terminal or $sp^3$ carbon atom, is replaced with an aryl radical. Typical arylalkyl groups include (but are not limited to) benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

The term "heteroarylalkyl" should be understood as referring to an acyclic alkyl radical in which one of the hydrogen atoms bonded to a carbon atom, typically a terminal or $sp^3$ carbon atom, is replaced with a heteroaryl radical. Typical heteroarylalkyl groups include (but are not limited to) 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 ring atoms, typically 1 to 3 heteroatoms selected from N, O, P, and S, with the remainder being carbon atoms. The heteroaryl moiety of the heteroarylalkyl group may be a monocycle having 3 to 7 ring members (2 to 6 carbon atoms) or a bicycle having 7 to 10 ring members (4 to 9 carbon atoms) and 1 to 3 heteroatoms selected from N, O, P, and S, for example: a bicyclo [4,5], [5,5], [5,6], or [6,6] system.

The term "alkynyl" should be understood as referring to a $C_2$-$C_{18}$ hydrocarbon containing normal, secondary, tertiary or cyclic carbon atoms with at least one site of unsaturation, i.e., a carbon-carbon, sp triple bond. Examples include, but are not limited to acetylenic (CCH) and propargyl ($CH_2CCH$). The term "alkynyl" should also be understood as referring to an alkynylene, an unsaturated, branched or straight chain or cyclic hydrocarbon radical of 2-18 carbon atoms, and having two monovalent radical centers derived by the removal of two hydrogen atoms from carbon atoms of a parent alkyne. Typical alkynylene radicals include (but are not limited to) acetylene (CC), propargyl ($CH_2CC$), and 4-pentynyl ($CH_2CH_2CH_2CC$).

The term "alkenyl" should be understood as referring to a $C_2$-$C_{18}$ hydrocarbon containing normal, secondary, tertiary or cyclic carbon atoms with at least one site of unsaturation, i.e., a carbon-carbon, $sp^2$ double bond. Examples include, but are not limited to ethylene or vinyl ($CH=CH_2$), allyl ($CH_2CH=CH_2$), cyclopentenyl ($C_5H7$), and 5-hexenyl ($CH_2CH_2CH_2CH_2CH=CH_2$). The term "alkenyl" should also be understood as referring to an alkenylene, an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to 1,2-ethylene (CH=CH).

In the context of this specification, the term "substituted", when used as adjective to "alkyl", "heteroalkyl", "cycloalkyl", "heterocycloalkyl", "aryl", "heteroaryl", "alkylaryl" and the like, indicates that said "alkyl", "heteroalkyl", "cycloalkyl", "heterocycloalkyl", "aryl", "alkylaryl" or "heteroaryl" group contains one or more substituents, which may include, but are not limited to, OH, =O, =S, NRh, =N—ORh, SH, $NH_2$, $NO_2$, NO, $N_3$, $CF_3$, CN, OCN, SCN, NCO, NCS, C(O)$NH_2$, C(O)H, C(O)OH, halogen, Rh, SRh, S(O)Rh, S(O)ORh, S(O)$_2$Rh, S(O)$_2$ORh, OS(O)Rh, OS(O)ORh, OS(O)$_2$Rh, OS(O)$_2$ORh, OP(O)(ORh)(ORi), P(O)(ORh)(ORi), ORh, NHRi, N(Rh)Ri, +N(Rh)(Ri)Rj, Si(Rh)(Ri)(Rj), C(O)Rh, C(O)ORh, C(O)N(Ri)Rh, OC(O)Rh, OC(O)ORh, OC(O)N(Rh)Ri, N(Ri)C(O)Rh, N(Ri)C(O)ORh, N(Ri)C(O)N(Rj)Rh, and the thio derivatives of these substituents, or a protonated or deprotonated form of any of these substituents, wherein Rh, Ri, and Rj are independently selected from H and optionally substituted $C_{1-15}$ alkyl, $C_{1-15}$ heteroalkyl, $C_{3-15}$ cycloalkyl, $C_{3-15}$ heterocycloalkyl, $C_{4-15}$ aryl, or $C_{4-15}$ heteroaryl or a combination thereof, two or more of Rh, Ri, and Rj optionally being joined to form one or more carbocycles or heterocycles.

The term "alkyl" as used herein may refer to a straight chain or branched, saturated or unsaturated hydrocarbon substituent. Examples of alkyl groups include, but are not limited to, methyl, ethyl, propyl, butyl, pentyl, hexyl, octyl, decyl, isopropyl, sec-butyl, isobutyl, tert-butyl, isopentyl, 2-methylbutyl, vinyl, allyl, 1-butenyl, 2-butenyl, isobutylenyl, 1-pentenyl, and 2-pentenyl.

The term "heteroalkyl" as used herein may refer to a straight chain or branched, saturated or unsaturated hydrocarbon substituent in which at least one carbon is replaced by a heteroatom. Examples include, but are not limited to, methyloxymethyl, ethyloxymethyl, methyloxyethyl, ethyloxyethyl, methylaminomethyl, dimethylaminomethyl, methylaminoethyl, dimethylaminoethyl, methylthiomethyl, ethylthiomethyl, ethylthioethyl, and methylthioethyl.

The term "cycloalkyl" as used herein may refer to a saturated or unsaturated non-aromatic carbocycle substituent, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

The term "heterocycloalkyl" as used herein may refer to a saturated or unsaturated non-aromatic cyclic hydrocarbon substituent, which may consist of one ring or two or more rings fused together, wherein at least one carbon in one of the rings is replaced by a heteroatom. Examples include, but are not limited to, tetrahydrofuranyl, pyrrolidinyl, piperidinyl, 1,4-dioxanyl, decahydroquinolinyl, piperazinyl, oxazolidinyl, and morpholinyl.

The term "heterocycloalkyl" as used herein may refer to a saturated or unsaturated non-aromatic cyclic hydrocarbon substituent, which may consist of one ring or two or more rings fused together, wherein at least one carbon in one of the rings is replaced by a heteroatom. Examples include, but are not limited to, tetrahydrofuranyl, pyrrolidinyl, piperidinyl, 1,4-dioxanyl, decahydroquinolinyl, piperazinyl, oxazolidinyl, and morpholinyl.

The term "alkylaryl" as used herein may refer to an aryl attached to an alkyl, wherein the terms alkyl and aryl are as defined above. Examples include, but are not limited to, benzyl and ethylbenzene radical.

The extension "-ylene" as opposed to "-yl" in for example "alkylene" as opposed to "alkyl" indicates that said for example "alkylene" is a divalent moiety connected to one or two other moieties via two covalent single bonds or one double bond as opposed to being a monovalent group connected to one moiety via one covalent single bond in said for example "alkyl". The term "alkylene" therefore may refer to a straight chain or branched, saturated or unsaturated hydrocarbon moiety; the term "heteroalkylene" as used herein may refer to a straight chain or branched, saturated or unsaturated hydrocarbon moiety in which at least one carbon is replaced by a heteroatom; the term "arylene" as used herein may refer to a carbocyclic aromatic moiety, which may consist of one ring or two or more rings fused together; the term "heteroarylene" as used herein may refer to a carbocyclic aromatic moiety, which may consist of one ring or two or more rings fused together, wherein at least one carbon in one of the rings is replaced by a heteroatom; the term "cycloalkylene" as used herein may refer to a saturated or unsaturated non-aromatic carbocycle moiety, which may consist of one ring or two or more rings fused together; the term "heterocycloalkylene" as used herein may refer to a saturated or unsaturated non-aromatic cyclic hydrocarbon moiety, which may consist of one ring or two or more rings fused together, wherein at least one carbon in one of the rings is replaced by a heteroatom. Exemplary divalent moieties include those examples given for the monovalent groups hereinabove in which one hydrogen atom is removed.

The prefix "poly" in "polyalkylene", "polyheteroalkylene", "polyarylene", "polyheteroarylene", polycycloalkylene", "polyheterocycloalkylene", and the like, indicates that two or more of such "-ylene" moieties, e.g., alkylene moieties, are joined together to form a branched or unbranched multivalent moiety containing one or more attachment sites for adjacent moieties.

In an embodiment, the alkyl group is unsubstituted or substituted $C_1$-$C_8$ alkyl, heteroalkyl, cycloalkyl, heterocycloalkyl, arylalkyl, heteroarylalkyl, alkynyl or alkenyl.

In an embodiment, $R_2$ is an aryl group.

The term "aryl" as used herein may refer to a carbocyclic aromatic substituent, which may consist of one ring or two or more rings fused together. Examples of aryl groups include, but are not limited to, phenyl, naphthyl, and anthracenyl.

The term "heteroaryl" as used herein may refer to a carbocyclic aromatic substituent, which may consist of one ring or two or more rings fused together, wherein at least one carbon in one of the rings is replaced by a heteroatom. Examples of heteroaryl groups include, but are not limited to, pyridinyl, furanyl, pyrrolyl, triazolyl, pyrazolyl, imidazolyl, thiophenyl, indolyl, benzofuranyl, benzimidazolyl, indazolyl, benzotriazolyl, benzisoxazolyl, and quinolinyl.

Certain linkers of the disclosure possess chiral centers or double bonds; the enantiomeric, diastereomeric, and geometric mixtures of two or more isomers, in any composition, as well as the individual isomers are encompassed within the scope of the present disclosure.

In an embodiment, the aryl group is aryl or heteroaryl.

In an embodiment, m is 0.

In an embodiment, Y is a saccharide and $R_3$ is a side chain of an amino acid.

In an embodiment, Y is β-D-glucose and $R_3$ is the side chain of an α-amino acid, serine, threonine or tyrosine.

In an embodiment, Y is β-D-glucose and $R_3$ is the side chain of serine.

In an embodiment, Y is a saccharide; $R_3$ is a side chain of an amino acid; and $R_2$ is H.

In an embodiment, Y is β-D-glucose; $R_3$ is the side chain of an α-amino acid, serine, threonine or tyrosine; and $R_2$ is H.

In an embodiment, Y is β-D-glucose; $R_3$ is the side chain of serine; and $R_2$ is H.

In an embodiment, m is 1.

In an embodiment, $R_1$ is an amino acid side chain.

In an embodiment, $R_1$ is selected from the group of side chains of α-amino acids, valine, phenylalanine, tyrosine, leusine, isoleusine, arginine, alanine, lysine and glycine.

In an embodiment, $R_1$ is selected from the group of side chains of valine, phenylalanine and alanine.

In an embodiment, $R_1$ is the side chain of valine.

In an embodiment, Y is a saccharide; $R_3$ is a side chain of an amino acid; $R_2$ is H; m=1; and $R_1$ is selected from the group of side chains of α-amino acids, valine, phenylalanine, tyrosine, leusine, isoleusine, arginine, alanine, lysine and glycine.

In an embodiment, Y is β-D-glucose; $R_3$ is the side chain of an α-amino acid, serine, threonine or tyrosine; $R_2$ is H; m=1; and $R_1$ is selected from the group of side chains of α-amino acids, valine, phenylalanine, tyrosine, leusine, isoleusine, arginine, alanine, lysine and glycine.

In an embodiment, Y is a saccharide; $R_3$ is the side chain of serine; $R_2$ is H; m=1; and $R_1$ is the side chain of valine.

In an embodiment, Y is β-D-glucose; $R_3$ is the side chain of serine; $R_2$ is H; m=1; and $R_1$ is the side chain of valine.

In an embodiment, Z is absent.

In an embodiment, Z comprises a self-immolative group.

In an embodiment, Z comprises a self-immolative group linking the linker of the present invention and the payload molecule. The term "self-immolative" refers to a functional chemical moiety that is capable of covalently linking together chemical moieties (e.g. MMAU to the linker of the present invention) and that will spontaneously separate from e.g. the MMAU or a cytotoxic drug if its bond to the rest of the linker is cleaved.

In an embodiment, the self-immolative group is para-aminobenzyloxycarbonyl (PABC), orto-aminobenzyloxycarbonyl, an α-amino acid and an oligopeptide. In an embodiment, the oligopeptide is di-, tri- or tetrapeptide of α-amino acids. Said group is capable of spontaneously cleaving itself from the conjugate after the linker has been cleaved by an enzyme.

In an embodiment, the self-immolative group is a para-aminobenzyloxycarbonyl (PABC) group.

In an embodiment, Y is a saccharide; $R_3$ is a side chain of an amino acid; $R_2$ is H; m=1; $R_1$ is selected from the group of side chains of α-amino acids, valine, phenylalanine, tyrosine, leusine, isoleusine, arginine, alanine, lysine and glycine; and Z is PABC.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; and Z is PABC.

In an embodiment, Y is a saccharide; $R_3$ is the side chain of serine; $R_2$ is H; m=1; $R_1$ is the side chain of valine; and Z is PABC.

In an embodiment, Y is β-D-glucose; $R_3$ is the side chain of serine; $R_2$ is H; m=1; $R_1$ is the side chain of valine; and Z is PABC.

In an embodiment, D is selected from the group consisting of a cytotoxic drug, an immunomodulatory agent, a labeling agent, a chelator and a radioactive agent.

In an embodiment, the immunomodulatory agent is selected from the group of corticosteroids such as cortisol, cortisone, prednisone, prednisolone, methylprednisolone, dexamethasone, betamethasone, triamcinolone, fludrocortisone and deoxycorticosterone, or an analogue thereof; and thalidomide, lenalidomide (CC-5013), CC-4047, or an analogue thereof. In an embodiment, the labeling agent is selected from the group of fluorescent label, magnetic label and isotope label.

In an embodiment, the chelator is selected from the group of NOTA, DOTA, TRAP and analogous chelators.

In an embodiment, the radioactive agent is selected from the group of positron emitter of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc.

In an embodiment, D is a cytotoxic drug selected from the group consisting of a tubulin-binding agent, a tubulin-disrupting agent, an auristatin, a DNA-binding agent and a DNA-alkylating and/or crosslinking agent.

In an embodiment, D is an auristatin.

In an embodiment, the auristatin is monomethylauristatin E (MMAE) saccharide conjugate of Formula AS.

Formula AS

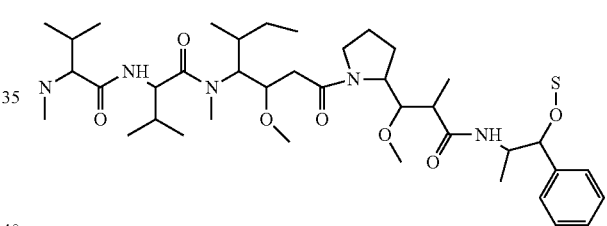

wherein S is a saccharide.

In an embodiment, the saccharide comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof.

In an embodiment, D is monomethylauristatin E β-D-glucuronide (MMAU).

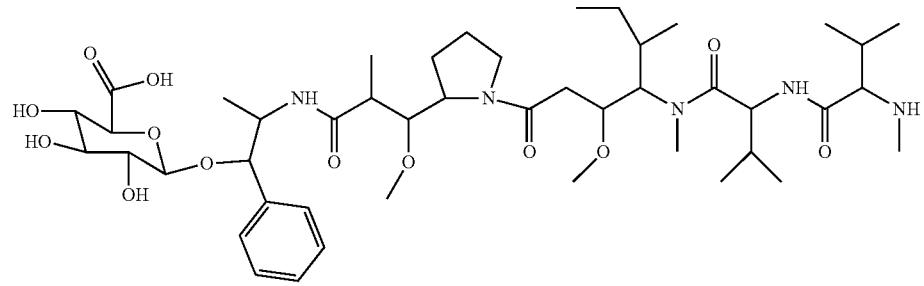

MMAU

In an embodiment, the payload molecule D comprises an amine moiety, through which the payload molecule is bound so as to form a secondary or tertiary amine.

In the context of this specification, the term "cytotoxic drug" may refer to any cytotoxic drug or cytotoxic drug derivative. It may also refer to the cytotoxic drug moiety of the conjugate according to one or more embodiments; said cytotoxic drug moiety may be modified as described in this specification, e.g. by the addition of a linker of the present invention. The term "cytotoxic drug" may also refer to a cytotoxic agent.

The cytotoxic drug may be any compound that results in the death of a cell, or induces cell death, or in some manner decreases cell viability. The cytotoxic drug can be any of many small molecule drugs, including, but not limited to, dolastatins; auristatins; epothilones; daunorubicins and doxorubicins; alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylene-phosphoramide, triethylenethiophosphaoramide and trimethylolomelamine; acetogenins (especially bullatacin and bullatacinone); camptothecins (including the synthetic analogue topotecan); bryostatin; callystatin; CC-1065 (including its adozelesin, carzelesin and bizelesin synthetic analogues); cryptophycins (particularly cryptophycin 1 and cryptophycin 8); duocarmycin (including the synthetic analogues, KW-2189 and CBI-TMI); eleutherobin; pancratistatin; sarcodictyins; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicins, especially calicheamicin yl; dynemicin, including dynemicin A; esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin; chromomycins, dactinomycin, detorubicin, 6-diazo-5-oxo-L-norleucine, other doxorubicin derivatives including morpho lino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-fluorouracil; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; maytansinoids, such as maytansine and N-glucosylmaytansinoids, ansamitocins, DM-1, DM-4; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; anti-hormonal agents that act to regulate or inhibit hormone action on tumours, such as anti-estrogens including for example tamoxifen, raloxifene, aromatase inhibiting 4(5)-imidazo les, 4-hydroxytamoxifen, trioxifene, keoxifene, LY117018, onapristone, and toremifene (Fareston); and anti-androgens, such as flutamide, nilutamide, bicalutamide, leuprolide, and goserelin; tubulysins; amanitins, such as α-amanitin; and pharmaceutically acceptable salts, acids; and saccharide derivatives of any of the above as disclosed in the International Patent Publication No. WO/2016/001485 the content of which is hereby incorporated in its entirety.

In an embodiment, the cytotoxic drug is a dolastatin, auristatin, doxorubicin, DM1, epirubicin, duocarmycin or any analogue or derivative thereof.

In an embodiment, the cytotoxic drug is a dolastatin, auristatin, doxorubicin, or any analogue or derivative thereof.

In an embodiment, the cytotoxic drug is dolastatin 10 or any derivative thereof.

In an embodiment, the cytotoxic drug is dolastatin 15 or any derivative thereof.

In an embodiment, the cytotoxic drug is auristatin F or any derivative thereof.

In an embodiment, the cytotoxic drug is dolastatin 10, dolastatin 15, or auristatin F.

In an embodiment, the cytotoxic drug is dolastatin 10.

In an embodiment, the cytotoxic drug is dolastatin 15.

In an embodiment, the cytotoxic drug is auristatin F.

Examples of suitable dolastatins include monomethyl and desmethyl dolastatins 10, 15, C, D and H, monomethyl and desmethyl isodolastatin H, and analogues and derivatives thereof. Dolastatins 10 and 15 are the most potent cytotoxic agents among the α-amino acidly occurring dolastatins. Monomethyl and desmethyl dolastatins 10 and 15 can be prepared by chemical synthesis according to standard peptide synthesis chemistry.

Examples of suitable auristatins that can be used include (but are not limited to) monomethyl and desmethyl auristatins E, F, EB, EFP, PY, PYE, PE, PHE, TP, 2-AQ and 6-AQ.

In an embodiment, the cytotoxic drug is daunorubicin or doxorubicin.

In an embodiment, the rubicin or the doxorubicin derivative is nemorubicin (3'-deamino-3'-[2"(S)-methoxy-4"-morpholinyl]doxorubicin; MMDX) or a modification or derivative thereof.

In an embodiment, the rubicin or the doxorubicin derivative is 3'-deamino-3",4'-anhydro-[2 "(S)-methoxy-3" (R)-oxy-4 "-morpho linyl] doxorubicin (PNU-159682) or a modification or derivative thereof.

In an embodiment, the rubicin or the doxorubicin derivative is PNU-EDA or a modification or derivative thereof.

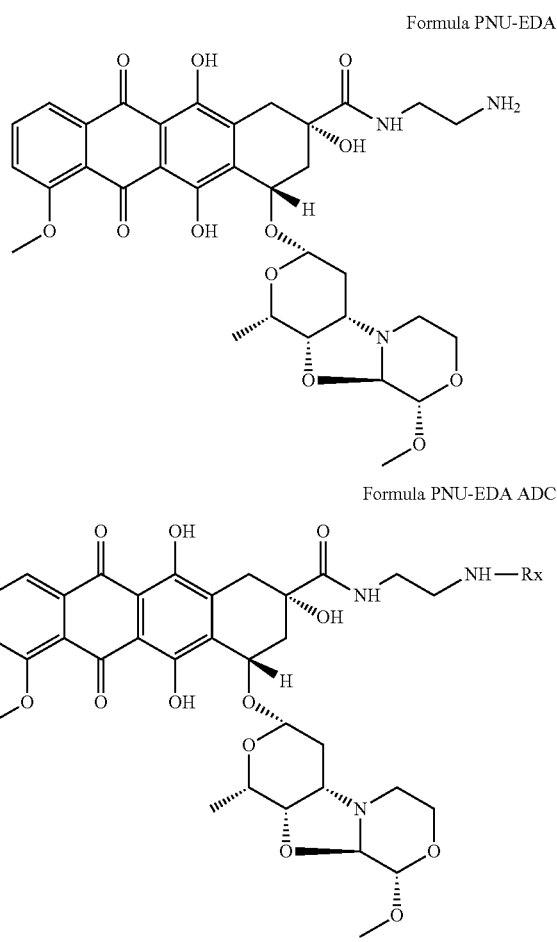

Formula PNU-EDA

Formula PNU-EDA ADC wherein Rx is X-L-Z-antibody and L is the linker described in this specification and X and Z are as described in this specification.

In an embodiment, the cytotoxic drug is a maytansinoid. The maytansinoid may be an N-glucosylmaytansinoid.

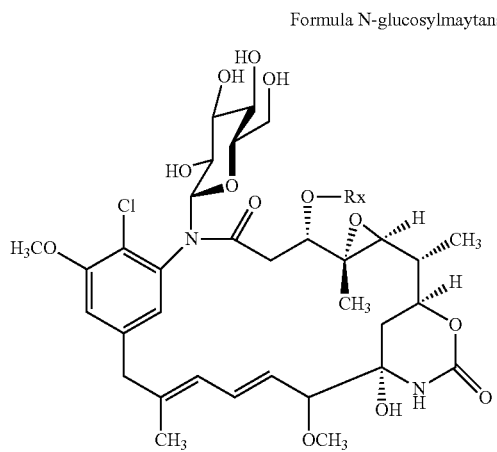

Formula N-glucosylmaytansinoid wherein Rx is X-L-Z-antibody and L is the linker described in this specification and X and Z are as described in this specification.

In an embodiment, the cytotoxic drug is maytansine, an ansamitocin, DM1 or DM4 (also known as DM-4).

In an embodiment, the cytotoxic drug is DM1. DM1 is also known as DM-1 and mertansine.

In an embodiment, the cytotoxic drug is a rubicin. Suitable rubicins may be e.g. daunorubicins, doxorubicins, detorubicin, other doxorubicin derivatives including morpholino-doxorubicin, cyanomorpholino-doxorubicin, 2-pyrrolino-doxorubicin, deoxydoxorubicin, epirubicin, esorubicin, idarubicin, rodorubicin, zorubicin, and pirarubicin.

In an embodiment, the cytotoxic drug is epirubicin.

In an embodiment, the cytotoxic drug is duocarmycin. Suitable duocarmyxins may be e.g. duocarmycin A, duocarmycin B1, duocarmycin B2, duocarmycin C1, duocarmycin C2, duocarmycin D, duocarmycin SA, duocarmycin MA, and CC-1065. The term "duocarmycin" should be understood as referring also to synthetic analogs of duocarmycins, such as adozelesin, bizelesin, carzelesin, KW-2189 and CBI-TMI.

In an embodiment, the cytotoxic drug comprises a duocarmycin fragment that can alkylate DNA. In an embodiment, the cytotoxic drug comprises two or more duocarmycin fragments that can alkylate DNA. In an embodiment, the cytotoxic drug comprises two duocarmycin fragments that can alkylate DNA.

In an embodiment, the duocarmycin is a duocarmycin-saccharide conjugate of Formula DS.

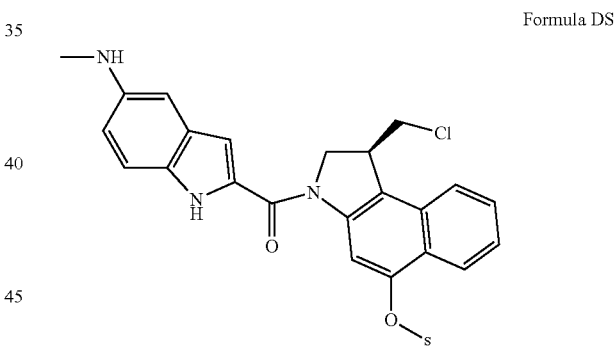

Formula DS wherein S is a saccharide.

In an embodiment, the saccharide comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof.

Examples of suitable dolastatins include monomethyl and desmethyl dolastatins 10, 15, C, D and H, monomethyl and desmethyl isodolastatin H, and analogues and derivatives thereof.

In an embodiment, the cytotoxic drug is a tubulysin.

In an embodiment, the cytotoxic drug is an amanitin, such as an α-amanitin.

In an embodiment, the cytotoxic drug is a cryptophycin.

In an embodiment, the auristatin is monomethylauristatin E.

In an embodiment, the auristatin is MMAU.

In an embodiment, the auristatin is monomethylauristatin F, W or M.

In an embodiment, the cytotoxic drug is a pyrrolobenzodiazepine (PBD), a PBD dimer or an analogue thereof.

In an embodiment, the pyrrolobenzodiazepine (PBD), a PBD dimer or an analogue thereof is selected from the group of naturally occurring and synthetic analogues, abbeymycin, chicamycin, DC-81; mazethramycin, neothramycins A and B, porothramycin, prothracarcin, sibanomicin (DC-102), sibiromycin and tomamycin.

In an embodiment, the pyrrolobenzodiazepine (PBD), a PBD dimer or an analogue thereof is a non-crosslinking analogue described in Miller et al. 2016, Mol Cancer Ther; 15(8); 1-9.

In an embodiment, Y is a saccharide; $R_3$ is a side chain of an amino acid; $R_2$ is H; m=1; $R_1$ is selected from the group of side chains of α-amino acids, valine, phenylalanine, tyrosine, leusine, isoleusine, arginine, alanine, lysine and glycine; Z is absent; and D is a cytotoxic drug.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; and D is a cytotoxic drug.

In an embodiment, Y is a saccharide; $R_3$ is the side chain of serine; $R_2$ is H; m=1; $R_1$ is the side chain of valine; Z is absent; and D is a cytotoxic drug.

In an embodiment, Y is β-D-glucose; $R_3$ is the side chain of serine; $R_2$ is H; m=1;

$R_1$ is the side chain of valine; Z is absent; and D is a cytotoxic drug.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is a cytotoxic drug.

In an embodiment, Y is a saccharide; $R_3$ is the side chain of serine; $R_2$ is H; m=1; $R_1$ is the side chain of valine; Z is PABC; and D is a cytotoxic drug.

In an embodiment, Y is β-D-glucose; $R_3$ is the side chain of serine; $R_2$ is H; m=1; $R_1$ is the side chain of valine; Z is PABC; and D is a cytotoxic drug.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is an auristatin.

In an embodiment, Y is a saccharide; $R_3$ is the side chain of serine; $R_2$ is H; m=1; $R_1$ is the side chain of valine; Z is PABC; and D is an auristatin.

In an embodiment, Y is β-D-glucose; $R_3$ is the side chain of serine; $R_2$ is H; m=1; $R_1$ is the side chain of valine; Z is PABC; and D is an auristatin.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is MMAU.

In an embodiment, Y is a saccharide; $R_3$ is the side chain of serine; $R_2$ is H; m=1; $R_1$ is the side chain of valine; Z is PABC; and D is MMAU.

In an embodiment, Y is β-D-glucose; $R_3$ is the side chain of serine; $R_2$ is H; m=1; $R_1$ is the side chain of valine; Z is PABC; and D is MMAU.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4.

In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, n is 5.

In an embodiment, n is 6.

In an embodiment, n is 7.

In an embodiment, n is 8.

In an embodiment, n is 9.

In an embodiment, X is absent.

In an embodiment, X is a spacer group.

The spacer group connects the linker of the present invention to the targeting unit. In an embodiment, the targeting unit is an antibody and the spacer group connects the linker to an amino acid side chain of the antibody with a covalent bond. In an embodiment, the covalent bond is an amide bond. In an embodiment, the covalent bond is a thioether bond. In an embodiment, the amino acid side chain of the antibody is the side chain of cysteine. In an embodiment, the amino acid side chain of the antibody is the side chain of lysine.

In an embodiment, X is selected from the group consisting of acyl group, alkyl group, aryl group, amino acid, and a bioorthogonal linking group.

In an embodiment, the spacer group comprises an acyl group conjugated to the rest of the linker with an amide bond.

In an embodiment, the spacer group comprises an alkyl group conjugated to the rest of the linker with an amine bond.

In an embodiment, the spacer group comprises a bioorthogonal linking group.

In an embodiment, the spacer group comprises a bioorthogonal linking group selected from the group consisting of azide, alkyne, triazole, maleimide, thiol, amine, carboxylic acid, amide, alkene, ether, thioether, aldehyde, ketone, hydroxylamine, hemiacetal, acetal, phosphine, tetrazine, cyclooctene, nitrone, isoxazo line, nitrile oxide, norbornene, oxanorbornadiene, tetrazole, pyrazo line and quadricyclane.

In an embodiment, the bioorthogonal linking group is a 1,3-triazole.

In an embodiment, the bioorthogonal linking group is an alkyne selected from the group of aliphatic alkyne such as a propargyl group or a cycloalkyne such as DBCO, DIBO, cyclononyne, cyclooctyne, and the like.

In an embodiment, the bioorthogonal linking group is an azide.

In the present specification and its embodiments, "a maleimide" refers to both an intact maleimide and a hydrolyzed maleimide connected to the targeting unit with a thioether bond. In an embodiment, the spacer group comprises a maleimide group.

In an embodiment, the spacer group comprises a hydrolyzed maleimide group.

In an embodiment, the spacer group comprises a maleimide group connected to the targeting unit with a thioether bond.

In an embodiment, the spacer group is maleimidopropionate or maleimiodohexanoate group.

In an embodiment, the spacer group comprises a hydrolyzed maleimide group connected to the targeting unit with a thioether bond.

In an embodiment, Y is a saccharide; $R_3$ is a side chain of an amino acid; $R_2$ is H; m=1; $R_1$ is selected from the group of side chains of α-amino acids, valine, phenylalanine, tyrosine, leusine, isoleusine, arginine, alanine, lysine and glycine; Z is absent; D is a cytotoxic drug; and X is an acyl group comprising a maleimide.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a cytotoxic drug; and X is an acyl group comprising a maleimide.

In an embodiment, Y is a saccharide; $R_3$ is the side chain of serine; $R_2$ is H; m=1; $R_1$ is the side chain of valine; Z is absent; D is a cytotoxic drug; and X is an acyl group comprising a maleimide.

In an embodiment, Y is β-D-glucose; $R_3$ is the side chain of serine; $R_2$ is H; m=1; $R_1$ is the side chain of valine; Z is absent; D is a cytotoxic drug; and X is an acyl group comprising a maleimide.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a cytotoxic drug; and X is an acyl group comprising a maleimide.

In an embodiment, Y is a saccharide; $R_3$ is the side chain of serine; $R_2$ is H; m=1; $R_1$ is the side chain of valine; Z is PABC; D is a cytotoxic drug; and X is an acyl group comprising a maleimide.

In an embodiment, Y is β-D-glucose; $R_3$ is the side chain of serine; $R_2$ is H; m=1; $R_1$ is the side chain of valine; Z is PABC; D is a cytotoxic drug; and X is an acyl group comprising a maleimide.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising a maleimide.

In an embodiment, Y is a saccharide; $R_3$ is the side chain of serine; $R_2$ is H; m=1; $R_1$ is the side chain of valine; Z is PABC; D is an auristatin; and X is an acyl group comprising a maleimide.

In an embodiment, Y is β-D-glucose; $R_3$ is the side chain of serine; $R_2$ is H; m=1; $R_1$ is the side chain of valine; Z is PABC; D is an auristatin; and X is an acyl group comprising a maleimide.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is MMAU; and X is an acyl group comprising a maleimide.

In an embodiment, Y is a saccharide; $R_3$ is the side chain of serine; $R_2$ is H; m=1; $R_1$ is the side chain of valine; Z is PABC; D is MMAU; and X is an acyl group comprising a maleimide.

In an embodiment, Y is β-D-glucose; $R_3$ is the side chain of serine; $R_2$ is H; m=1; $R_1$ is the side chain of valine; Z is PABC; D is MMAU; and X is an acyl group comprising a maleimide.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4.

In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, n is 5.

In an embodiment, n is 6.

In an embodiment, n is 7.

In an embodiment, n is 8.

In an embodiment, n is 9.

In an embodiment, the targeting unit T is a molecule that specifically binds to a target molecule. In the context of the present invention, the specific binding has the meaning that the targeting molecule has a reasonably higher binding affinity to its target than to unrelated molecules. An example of the specific binding is the binding of an antibody to its target epitope.

In an embodiment, the targeting unit T is a molecule that specifically binds to a target molecule on a surface of a target cell.

In an embodiment, the targeting unit T is small-molecule weight ligand, a lectin, a peptide, an aptamer, or an antibody.

In an embodiment, the targeting unit T is an antibody.

The antibody may, in principle, be any antibody or its binding fragment, for instance an IgG, an scFv, a single domain antibody, an Fv, a VHH antibody, a diabody, a tandem diabody, a Fab, a Fab', a F(ab')2, a Db, a dAb-Fc, a taFv, a scDb, a dAb2, a DVD-Ig, a Bs(scFv)4-IgG, a taFv-Fc, a scFv-Fc-scFv, a Db-Fc, a scDb-Fc, a scDb-CH$_3$, or a dAb-Fc-dAb.

In an embodiment, the antibody is a human antibody or a humanized antibody. In this context, the term "human antibody", as it is commonly used in the art, is to be understood as meaning antibodies having variable regions in which both the framework and complementary determining regions (CDRs) are derived from sequences of human origin. In this context, the term "humanized antibody", as it is commonly used in the art, is to be understood as meaning antibodies wherein residues from a CDR of an antibody of human origin are replaced by residues from a CDR of a nonhuman species (such as mouse, rat or rabbit) having the desired specificity, affinity and capacity.

In an embodiment, the antibody is capable of binding a cell surface antigen.

In an embodiment, the cell surface antigen is a tumor antigen and/or a cancer antigen.

In an embodiment, the antibody is selected from the group consisting of bevacizumab, tositumomab, etanercept, trastuzumab, adalimumab, alemtuzumab, gemtuzumab ozogamicin, efalizumab, rituximab, infliximab, abciximab, basiliximab, palivizumab, omalizumab, daclizumab, cetuximab, panitumumab, epratuzumab, 2G12, lintuzumab, nimotuzumab and ibritumomab tiuxetan.

In an embodiment, the antibody is capable of binding a target molecule selected from the group consisting of CD2, CD3, CD4, CD5, CD6, CD11, CD8, CD11a, CD19, CD20, CD22, CD25, CD26, CD30, CD33, CD34, CD37, CD38, CD40, CD44, CD46, CD52, CD56, CD79, CD105, CD138, epidermal growth factor receptor 1 (EGFR), epidermal growth factor receptor 2 (HER2/neu), HER3 or HER4 receptor, LFA-1, Macl, p150.95, VLA-4, ICAM-1, VCAM, EpCAM, alpha4/beta7 integrin, alpha v/beta3 integrin including either alpha or beta subunits thereof (e.g. anti-CD11a, anti-CD18 or anti-CD11 b antibodies), tissue factor (TF), tumor necrosis factor alpha (TNF-α), human vascular endothelial growth factor (VEGF), glycoprotein IIb/IIIa, TGF-beta, alpha interferon (alpha-IFN), IL-8, IL-2 receptor, IgE, respiratory syncytial virus (RSV), HIV-1 envelope glycoprotein gp120, cancer-associated high-mannose type N-glycans, blood group antigen Apo2, death receptor, flk2/flt3 receptor, obesity (OB) receptor, mpl receptor, CTLA-4, transferrin receptor, Lewis y, GD3 and protein C.

In an embodiment, the antibody is selected from the group consisting of abagovomab, actoxumab, adecatumumab, afutuzumab, altumomab, amatuximab, anifrolumab, apolizumab, atinumab, atlizumab, atorolimumab, bapineuzumab, basiliximab, bavituximab, belimumab, benralizumab, bertilimumab, besilesomab, bezlotoxumab, bimagrumab, bivatuzumab, blinatumomab, blosozumab, brentuximab, briakinumab, brodalumab, canakinumab, cantuzumab, caplacizumab, capromab, carlumab, catumaxomab, CC49, cedelizumab, cixutumumab, clazakizumab, clenoliximab, clivatuzumab, conatumumab, concizumab, crenezumab, CR6261, dacetuzumab, dalotuzumab, daratumumab, demcizumab, denosumab, detumomab, drozitumab, duligotumab, dupilumab, dusigitumab, ecromeximab, eculizumab, edobacomab, edrecolomab, eldelumab, elotuzumab, elsilimomab, enavatuzumab, enlimomab, enokizumab, enoticumab, ensituximab, epitumomab, epratuzumab, ertumaxomab, etaracizumab, etrolizumab, evolocumab, exbivirumab, fanolesomab, faralimomab, farletuzumab, fasinumab, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gevokizumab, girentuximab, glembatumumab, golimumab, gomiliximab, guselkumab, ibalizumab, icrucumab, imciromab, imgatuzumab, inclacumab, indatuximab, intetumumab, inolimomab, inotuzumab, ipilimumab, iratumumab, itolizumab, ixekizumab, keliximab, labetuzumab, lambrolizumab, lampalizumab, lebrikizumab, lemalesomab, lerdelimumab, lexatumumab, libivirumab, ligelizumab, lintuzumab, lirilumab, lodelcizumab, lorvotuzumab, lucatumumab, lumiliximab, mapatumumab, margetuximab, maslimomab, mavrilimumab, matuzumab, mepolizumab, metelimumab, milatuzumab, minretumomab, mitumomab, mogamulizumab, morolimumab, motavizumab, moxetumomab, muromonab, namilumab, narnatumab, natalizumab, nebacumab, necitumumab, nerelimomab, nesvacumab, nimotuzumab, nivolumab, obinutuzumab, ocaratuzumab, ocrelizumab, odulimomab, ofatumumab, olaratumab, olokizumab, onartuzumab, oregovomab, orticumab, otelixizumab, oxelumab, ozanezumab, ozoralizumab, pagibaximab, panobacumab, parsatuzumab, pascolizumab, pateclizumab, patritumab, pemtumomab, perakizumab, pertuzumab, pidilizumab, pinatuzumab, pintumomab, placulumab, polatuzumab, ponezumab, priliximab, pritoxaximab, pritumumab, quilizumab, racotumomab, radretumab, rafivirumab, ramucirumab, raxibacumab, regavirumab, reslizumab, rilotumumab, robatumumab, roledumab, romosozumab, rontalizumab, rovelizumab, ruplizumab, samalizumab, sarilumab, satumomab, secukinumab, seribantumab, setoxaximab, sevirumab, sibrotuzumab, sifalimumab, siltuximab, simtuzumab, siplizumab, sirukumab, solanezumab, solitomab, sonepcizumab, sontuzumab, stamulumab, suvizumab, tabalumab, tacatuzumab, talizumab, tanezumab, taplitumomab, tefibazumab, tenatumomab, teneliximab, teplizumab, teprotumumab, TGN1412, ticilimumab, tildrakizumab, tiga-tuzumab, tocilizumab, toralizumab, tovetumab, tralokinumab, TRBS07, tregalizumab, tremelimumab, tucotuzumab, tuvirumab, ublituximab, urelumab, urtoxazumab, ustekinumab, vanticumab, vapaliximab, vatelizumab, vedolizumab, veltuzumab, vepalimomab, vesencumab, visilizumab, volociximab, vorsetuzumab, votumumab, zalutumumab, zanolimumab, zatuximab, ziralimumab, 2G12 (anti-HIV-1 envelope glycoprotein gp120), and zolimomab.

In an embodiment, the antibody is selected from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the antibody is an anti-EGFR antibody.

In an embodiment, an anti-EGFR1 antibody is cetuximab, imgatuzumab, matuzumab, nimotuzumab, necitumumab, panitumumab, or zalutumumab.

In an embodiment, the antibody is an epidermal growth factor receptor 2 (HER2/neu) antibody.

In an embodiment, an anti-HER2 antibody is margetuximab, pertuzumab, trastuzumab, ertumaxomab, and 520C9XH22.

In an embodiment, the antibody is an anti-CD22 antibody.

In an embodiment, an anti-CD22 antibody is bectumomab, moxetumomab, epratuzumab, inotuzumab, or pinatuzumab.

In an embodiment, the antibody is an anti-CD30 antibody.

In an embodiment, an anti-CD30 antibody is brentuximab vedotin (or the antibody portion of the brentuximab vedotin) or iratumumab.

In an embodiment, the antibody is an anti-CD33 antibody.

In an embodiment, an anti-CD33 antibody is gemtuzumab, SGN-CD33A or lintuzumab.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4.

In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, n is 5.

In an embodiment, n is 6.

In an embodiment, n is 7.

In an embodiment, n is 8.

In an embodiment, n is 9.

In an embodiment, n, or drug-to-antibody (DAR) ratio, of a targeting unit-linker-payload conjugate may be determined using a MALDI-TOF MS.

In an embodiment, n, or drug-to-antibody ratio, of a targeting unit-linker-payload conjugate may be determined using an ESI-MS.

Exemplary methods to determine n, or drug-to-antibody ratio, is described in Chen J, Yin S, Wu Y, Ouyang J. Development of a native nanoelectrospray mass spectrometry method for determination of the drug-to-antibody ratio of antibody-drug conjugates. Anal Chem. 2013 Feb. 5; 85(3):1699-1704. doi:10.1021/ac302959p.

In an embodiment, T is an antibody; n is between 1 and about 20; Y is a saccharide; $R_3$ is a side chain of an amino acid; $R_2$ is H; m=1; $R_1$ is selected from the group of side chains of α-amino acids, valine, phenylalanine, tyrosine, leusine, isoleucine, arginine, alanine, lysine and glycine; Z is absent; D is a cytotoxic drug; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleucine, arginine, alanine, lysine and glycine; Z is absent; D is a cytotoxic drug; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is absent; D is a cytotoxic drug; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of serine; $R_2$ is H; m=1; $R_1$ is the side chain of valine; Z is absent; D is a cytotoxic drug; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a cytotoxic drug; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is PABC; D is a cytotoxic drug; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is a cytotoxic drug; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is PABC; D is an auristatin; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is an auristatin; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is MMAU; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is PABC; D is MMAU; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is MMAU; and X is an acyl group comprising a maleimide connected to a cysteine side chain of the antibody via a thioether bond.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4.

In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, n is 5.

In an embodiment, n is 6.

In an embodiment, n is 7.

In an embodiment, n is 8.

In an embodiment, n is 9.

In an embodiment, the payload molecule D and the antibody are bound indirectly via the linker of the present invention.

In an embodiment, the cytotoxic drug and the antibody are bound indirectly via the linker of the present invention.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; and D is a cytotoxic drug.

In an embodiment, Y is β-D-glucuronic acid; $R_3$ is the side chain of serine; $R_2$ is H; m=1; $R_1$ is the side chain of valine; Z is absent; and D is a cytotoxic drug.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is a cytotoxic drug.

In an embodiment, Y is β-D-glucuronic acid; $R_3$ is the side chain of serine; $R_2$ is H; m=1; $R_1$ is the side chain of valine; Z is PABC; and D is a cytotoxic drug.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is an auristatin.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is a rubicin or a doxorubicin derivative.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; and D is a rubicin or a doxorubicin derivative.

In an embodiment, Y is a saccharide; $R_3$ is the side chain of serine; $R_2$ is H; m=1; $R_1$ is the side chain of valine; Z is PABC; and D is a rubicin or a doxorubicin derivative.

In an embodiment, Y is a saccharide; $R_3$ is the side chain of serine; $R_2$ is H; m=1; $R_1$ is the side chain of valine; Z is absent; and D is a rubicin or a doxorubicin derivative.

In an embodiment, Y is β-D-glucuronic acid; $R_3$ is the side chain of serine; $R_2$ is H; m=1; $R_1$ is the side chain of valine; Z is PABC; and D is an auristatin.

In an embodiment, Y is β-D-glucose; $R_3$ is the side chain of serine; $R_2$ is H; m=1; $R_1$ is the side chain of valine; Z is PABC; and D is a rubicin or a doxorubicin derivative.

In an embodiment, Y is β-D-glucose; $R_3$ is the side chain of serine; $R_2$ is H; m=1; $R_1$ is the side chain of valine; Z is absent; and D is a rubicin or a doxorubicin derivative.

In an embodiment, Y is β-D-glucuronic acid; $R_3$ is the side chain of serine; $R_2$ is H; m=1; $R_1$ is the side chain of valine; Z is PABC; and D is a rubicin or a doxorubicin derivative.

In an embodiment, Y is β-D-glucuronic acid; $R_3$ is the side chain of serine; $R_2$ is H; m=1; $R_1$ is the side chain of valine; Z is absent; and D is a rubicin or a doxorubicin derivative.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is MMAU.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is PNU-EDA.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; and D is PNU-EDA.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; and D is PNU-EDA.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; and D is PNU-EDA.

In an embodiment, Y is a saccharide; $R_3$ is the side chain of serine; $R_2$ is H; m=1; $R_1$ is the side chain of valine; Z is PABC; and D is PNU-EDA.

In an embodiment, Y is a saccharide; $R_3$ is the side chain of serine; $R_2$ is H; m=1; $R_1$ is the side chain of valine; Z is absent; and D is PNU-EDA.

In an embodiment, Y is β-D-glucuronic acid; $R_3$ is the side chain of serine; $R_2$ is H; m=1; $R_1$ is the side chain of valine; Z is PABC; and D is MMAU.

In an embodiment, Y is β-D-glucose; $R_3$ is the side chain of serine; $R_2$ is H; m=1; $R_1$ is the side chain of valine; Z is PABC; and D is PNU-EDA.

In an embodiment, Y is β-D-glucuronic acid; $R_3$ is the side chain of serine; $R_2$ is H; m=1; $R_1$ is the side chain of valine; Z is PABC; and D is PNU-EDA.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a cytotoxic drug; and X is an acyl group comprising a maleimide.

In an embodiment, Y is β-D-glucuronic acid; $R_3$ is the side chain of serine; $R_2$ is H; m=1; $R_1$ is the side chain of valine; Z is absent; D is a cytotoxic drug; and X is an acyl group comprising a maleimide.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a cytotoxic drug; and X is an acyl group comprising a maleimide.

In an embodiment, Y is β-D-glucuronic acid; $R_3$ is the side chain of serine; $R_2$ is H; m=1; $R_1$ is the side chain of valine; Z is PABC; D is a cytotoxic drug; and X is an acyl group comprising a maleimide.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising a maleimide.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a rubicin or a doxorubicin derivative; and X is an acyl group comprising a maleimide.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a rubicin or a doxorubicin derivative; and X is an acyl group comprising a maleimide.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a rubicin or a doxorubicin derivative; and X is an acyl group comprising a maleimide.

In an embodiment, Y is β-D-glucuronic acid; $R_3$ is the side chain of an α-amino acid, serine, threonine or tyrosine;

$R_2$ is H; m=1; $R_1$ is selected from the group of side chains of α-amino acids, valine, phenylalanine, tyrosine, leusine, isoleusine, arginine, alanine, lysine and glycine; Z is absent; D is a rubicin or a doxorubicin derivative; and X is an acyl group comprising a maleimide.

In an embodiment, Y is a saccharide; $R_3$ is the side chain of serine; $R_2$ is H; m=1; $R_1$ is the side chain of valine; Z is PABC; D is a rubicin or a doxorubicin derivative; and X is an acyl group comprising a maleimide.

In an embodiment, Y is a saccharide; $R_3$ is the side chain of serine; $R_2$ is H; m=1; $R_1$ is the side chain of valine; Z is absent; D is a rubicin or a doxorubicin derivative; and X is an acyl group comprising a maleimide.

In an embodiment, Y is β-D-glucose; $R_3$ is the side chain of serine; $R_2$ is H; m=1; $R_1$ is the side chain of valine; Z is absent; D is a rubicin or a doxorubicin derivative; and X is an acyl group comprising a maleimide.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is PNU-EDA; and X is an acyl group comprising a maleimide.

In an embodiment, Y is β-D-glucuronic acid; $R_3$ is the side chain of serine; $R_2$ is H; m=1; $R_1$ is the side chain of valine; Z is absent; D is a rubicin or a doxorubicin derivative; and X is an acyl group comprising a maleimide.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is PNU-EDA; and X is an acyl group comprising a maleimide.

In an embodiment, Y is β-D-glucose; $R_3$ is the side chain of serine; $R_2$ is H; m=1; $R_1$ is the side chain of valine; Z is PABC; D is a rubicin or a doxorubicin derivative; and X is an acyl group comprising a maleimide.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is PNU-EDA; and X is an acyl group comprising a maleimide.

In an embodiment, Y is β-D-glucuronic acid; $R_3$ is the side chain of serine; $R_2$ is H; m=1; $R_1$ is the side chain of valine; Z is PABC; D is a rubicin or a doxorubicin derivative; and X is an acyl group comprising a maleimide.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is PNU-EDA; and X is an acyl group comprising a maleimide.

In an embodiment, Y is β-D-glucuronic acid; $R_3$ is the side chain of serine; $R_2$ is H; m=1; $R_1$ is the side chain of valine; Z is PABC; D is an auristatin; and X is an acyl group comprising a maleimide.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is MMAU; and X is an acyl group comprising a maleimide.

In an embodiment, Y is a saccharide; $R_3$ is the side chain of serine; $R_2$ is H; m=1; $R_1$ is the side chain of valine; Z is PABC; D is PNU-EDA; and X is an acyl group comprising a maleimide.

In an embodiment, Y is a saccharide; $R_3$ is the side chain of serine; $R_2$ is H; m=1; $R_1$ is the side chain of valine; Z is absent; D is PNU-EDA; and X is an acyl group comprising a maleimide.

In an embodiment, Y is β-D-glucuronic acid; $R_3$ is the side chain of serine; $R_2$ is H; m=1; $R_1$ is the side chain of valine; Z is PABC; D is MMAU; and Xis an acyl group comprising a maleimide.

In an embodiment, Y is β-D-glucose; $R_3$ is the side chain of serine; $R_2$ is H; m=1; $R_1$ is the side chain of valine; Z is PABC; D is PNU-EDA; and X is an acyl group comprising a maleimide.

In an embodiment, Y is β-D-glucuronic acid; $R_3$ is the side chain of serine; $R_2$ is H; m=1; $R_1$ is the side chain of valine; Z is PABC; D is PNU-EDA; and X is an acyl group comprising a maleimide.

In an embodiment, Y is β-D-glucose; $R_3$ is the side chain of serine; $R_2$ is H; m=1; $R_1$ is the side chain of valine; Z is absent; D is PNU-EDA; and X is an acyl group comprising a maleimide.

In an embodiment, Y is β-D-glucuronic acid; $R_3$ is the side chain of serine; $R_2$ is H; m=1; $R_1$ is the side chain of valine; Z is absent; D is PNU-EDA; and X is an acyl group comprising a maleimide.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a cytotoxic drug; and X is an acyl group comprising an azide-reactive group.

In an embodiment, Y is β-D-glucuronic acid; $R_3$ is the side chain of serine; $R_2$ is H; m=1; $R_1$ is the side chain of valine; Z is absent; D is a cytotoxic drug; and X is an acyl group comprising a azide-reactive group.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a cytotoxic drug; and X is an acyl group comprising a azide-reactive group.

In an embodiment, Y is β-D-glucuronic acid; $R_3$ is the side chain of serine; $R_2$ is H; m=1; $R_1$ is the side chain of valine; Z is PABC; D is a cytotoxic drug; and X is an acyl group comprising a azide-reactive group.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising a azide-reactive group. In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a rubicin or a doxorubicin derivative; and X is an acyl group comprising a azide-reactive group.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a rubicin or a doxorubicin derivative; and X is an acyl group comprising a azide-reactive group.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a rubicin or a doxorubicin derivative; and X is an acyl group comprising a azide-reactive group.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a rubicin or a doxorubicin derivative; and X is an acyl group comprising a azide-reactive group.

In an embodiment, Y is a saccharide; $R_3$ is the side chain of serine; $R_2$ is H; m=1; $R_1$ is the side chain of valine; Z is PABC; D is a rubicin or a doxorubicin derivative; and X is an acyl group comprising a azide-reactive group.

In an embodiment, Y is a saccharide; $R_3$ is the side chain of serine; $R_2$ is H; m=1; $R_1$ is the side chain of valine; Z is absent; D is a rubicin or a doxorubicin derivative; and X is an acyl group comprising a azide-reactive group.

In an embodiment, Y is β-D-glucose; $R_3$ is the side chain of serine; $R_2$ is H; m=1; $R_1$ is the side chain of valine; Z is absent; D is a rubicin or a doxorubicin derivative; and X is an acyl group comprising a azide-reactive group.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is PNU-EDA; and X is an acyl group comprising a azide-reactive group.

In an embodiment, Y is β-D-glucuronic acid; $R_3$ is the side chain of serine; $R_2$ is H; m=1; $R_1$ is the side chain of valine; Z is absent; D is a rubicin or a doxorubicin derivative; and X is an acyl group comprising a azide-reactive group.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is PNU-EDA; and X is an acyl group comprising a azide-reactive group.

In an embodiment, Y is β-D-glucose; $R_3$ is the side chain of serine; $R_2$ is H; m=1; $R_1$ is the side chain of valine; Z is PABC; D is a rubicin or a doxorubicin derivative; and X is an acyl group comprising an azide-reactive group.

In an embodiment, Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is PNU-EDA; and X is an acyl group comprising an azide-reactive group.

In an embodiment, Y is β-D-glucuronic acid; $R_3$ is the side chain of serine; $R_2$ is H; m=1; $R_1$ is the side chain of valine; Z is PABC; D is a rubicin or a doxorubicin derivative; and X is an acyl group comprising an azide-reactive group.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is PNU-EDA; and X is an acyl group comprising an azide-reactive group.

In an embodiment, Y is β-D-glucuronic acid; $R_3$ is the side chain of serine; $R_2$ is H; m=1; $R_1$ is the side chain of valine; Z is PABC; D is an auristatin; and X is an acyl group comprising an azide-reactive group.

In an embodiment, Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is MMAU; and X is an acyl group comprising an azide-reactive group.

In an embodiment, Y is a saccharide; $R_3$ is the side chain of serine; $R_2$ is H; m=1; $R_1$ is the side chain of valine; Z is PABC; D is PNU-EDA; and X is an acyl group comprising an azide-reactive group.

In an embodiment, Y is a saccharide; $R_3$ is the side chain of serine; $R_2$ is H; m=1; $R_1$ is the side chain of valine; Z is absent; D is PNU-EDA; and X is an acyl group comprising an azide-reactive group.

In an embodiment, Y is β-D-glucuronic acid; $R_3$ is the side chain of serine; $R_2$ is H; m=1; $R_1$ is the side chain of valine; Z is PABC; D is MMAU; and X is an acyl group comprising an azide-reactive group.

In an embodiment, Y is β-D-glucose; $R_3$ is the side chain of serine; $R_2$ is H; m=1; $R_1$ is the side chain of valine; Z is PABC; D is PNU-EDA; and X is an acyl group comprising an azide-reactive group.

In an embodiment, Y is β-D-glucuronic acid; $R_3$ is the side chain of serine; $R_2$ is H; m=1; $R_1$ is the side chain of valine; Z is PABC; D is PNU-EDA; and X is an acyl group comprising an azide-reactive group.

In an embodiment, Y is β-D-glucose; $R_3$ is the side chain of serine; $R_2$ is H; m=1; $R_1$ is the side chain of valine; Z is absent; D is PNU-EDA; and X is an acyl group comprising an azide-reactive group.

In an embodiment, Y is β-D-glucuronic acid; $R_3$ is the side chain of serine; $R_2$ is H; m=1; $R_1$ is the side chain of valine; Z is absent; D is PNU-EDA; and X is an acyl group comprising an azide-reactive group.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a cytotoxic drug; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a cytotoxic drug; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a cytotoxic drug; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is absent; D is a cytotoxic drug; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of serine; $R_2$ is H; m=1; $R_1$ is the side chain of valine; Z is absent; D is a cytotoxic drug; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of serine; $R_2$ is H; m=1; $R_1$ is the side chain of valine; Z is absent; D is a cytotoxic drug; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of serine; $R_2$ is H; m=1; $R_1$ is the side chain of valine; Z is absent; D is a cytotoxic drug; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a cytotoxic drug; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a cytotoxic drug; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a cytotoxic drug; and X is an acyl group comprising an azide-reactive group connected to an azide group in the antibody via a 1,3-triazole.

In an embodiment, T is an antibody; n is between 1 and about 20; Y is a saccharide; $R_3$ is the side chain of serine; $R_2$ is H; m=1; $R_1$ is the side chain of valine; Z is PABC; D is a cytotoxic drug; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is a cytotoxic drug; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is a cytotoxic drug; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is a cytotoxic drug; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising an azide-reactive group connected to an azide group in the antibody via a 1,3-triazole. In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is an auristatin; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a rubicin or a doxorubicin derivative; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a rubicin or a doxorubicin derivative; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a rubicin or a doxorubicin derivative; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a rubicin or a doxorubicin derivative; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is a saccharide; $R_3$ is the side chain of serine; $R_2$ is H; m=1; $R_1$ is the side chain of valine; Z is PABC; D is an auristatin; and X is an acyl group comprising an azide-reactive group connected to an azide group in the antibody via a 1,3-triazole.

In an embodiment, T is an antibody; n is between 1 and about 20; Y is a saccharide; $R_3$ is the side chain of serine; $R_2$ is H; m=1; $R_1$ is the side chain of valine; Z is PABC; D is a rubicin or a doxorubicin derivative; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is absent; D is a rubicin or a doxorubicin derivative; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is PABC; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is a saccharide; $R_3$ is the side chain of serine; $R_2$ is H; m=1; $R_1$ is the side chain of valine; Z is absent; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is an auristatin; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is an auristatin; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is an auristatin; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is a rubicin or a doxorubicin derivative; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of serine; $R_2$ is H; m=1; $R_1$ is the side chain of valine; Z is absent; D is a rubicin or a doxorubicin derivative; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of serine; $R_2$ is H; m=1; $R_1$ is the side chain of valine; Z is absent; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is a rubicin or a doxorubicin derivative; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of serine; $R_2$ is H; m=1; $R_1$ is the side chain of valine; Z is absent; D is a rubicin or a doxorubicin derivative; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of serine; $R_2$ is H; m=1; $R_1$ is the side chain of valine; Z is absent; D is a rubicin or a doxorubicin derivative; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leucine, isoleusine, arginine, alanine, lysine and glycine; Z is PABC; D is MMAU; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leucine, isoleusine, arginine, alanine, lysine and glycine; Z is PABC; D is MMAU; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leucine, isoleusine, arginine, alanine, lysine and glycine; Z is PABC; D is MMAU; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is PNU-EDA; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is PNU-EDA; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is PNU-EDA; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is PNU-EDA; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is PNU-EDA; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is PNU-EDA; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is PABC; D is PNU-EDA; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of an α-amino acid, serine, threonine or tyrosine; $R_2$ is H; m=1; $R_1$ is selected from the group of side chains of α-amino acids, valine, phenylalanine, tyrosine, leusine, isoleusine, arginine, alanine, lysine and glycine; Z is absent; D is PNU-EDA; and X is an acyl group comprising an azide-reactive group connected to an azide group in the antibody via a 1,3-triazole.

In an embodiment, T is an antibody; n is between 1 and about 20; Y is a saccharide; $R_3$ is the side chain of serine; $R_2$ is H; m=1; $R_1$ is the side chain of valine; Z is PABC; D is MMAU; and X is an acyl group comprising an azide-reactive group connected to an azide group in the antibody via a 1,3-triazole.

In an embodiment, T is an antibody; n is between 1 and about 20; Y is a saccharide; $R_3$ is the side chain of serine; $R_2$ is H; m=1; $R_1$ is the side chain of valine; Z is PABC; D is PNU-EDA; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is PABC; D is PNU-EDA; and X is an acyl group comprising an azide-reactive group connected to an azide group in the antibody via a 1,3-triazole.

In an embodiment, T is an antibody; n is between 1 and about 20; Y is a saccharide; $R_3$ is the side chain of serine; $R_2$ is H; m=1; $R_1$ is the side chain of valine; Z is absent; D is PNU-EDA; and X is an acyl group comprising a maleimide connected to a cysteine side chain of the antibody via a thioether bond.

In an embodiment, T is an antibody; n is between 1 and about 20; Y is a saccharide; $R_3$ is the side chain of serine; $R_2$ is H; m=1; $R_1$ is the side chain of valine; Z is absent; D is PNU-EDA; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is MMAU; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is MMAU; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is MMAU; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is PNU-EDA; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of serine; $R_2$ is H; m=1; $R_1$ is the side chain of valine; Z is absent; D is PNU-EDA; and X is an acyl group comprising a maleimide connected to a cysteine side chain of the antibody via a thioether bond.

In an embodiment, T is an antibody; n is between 1 and about 20; Y is β-D-glucose; $R_3$ is the side chain of serine; $R_2$ is H; m=1; $R_1$ is the side chain of valine; Z is PABC; D is PNU-EDA; and X is an acyl group comprising an azide-reactive group connected to an azide group in the antibody via a 1,3-triazole.

In an embodiment, T is an antibody; n is between 1 and about 20; Y is β-D-glucose; $R_3$ is the side chain of serine; $R_2$ is H; m=1; $R_1$ is the side chain of valine; Z is absent; D is PNU-EDA; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is PNU-EDA; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of serine; $R_2$ is H; m=1; $R_1$ is the side chain of valine; Z is absent; D is PNU-EDA; and X is an acyl group comprising a maleimide connected to a cysteine side chain of the antibody via a thioether bond.

In an embodiment, T is an antibody; n is between 1 and about 20; Y is β-D-glucuronic acid; $R_3$ is the side chain of serine; $R_2$ is H; m=1; $R_1$ is the side chain of valine; Z is PABC; D is PNU-EDA; and X is an acyl group comprising an azide-reactive group connected to an azide group in the antibody via a 1,3-triazole.

In an embodiment, T is an antibody; n is between 1 and about 20; Y is β-D-glucuronic acid; $R_3$ is the side chain of serine; $R_2$ is H; m=1; $R_1$ is the side chain of valine; Z is absent; D is PNU-EDA; and X is an acyl group comprising an azide-reactive group connected to an azide group in the antibody via a 1,3-triazole.

In an embodiment, the linker-payload conjugate comprises the linker-payload conjugate according to Formula IIIb, Formula IIIc or Formula IIId, wherein D is a cytotoxic drug.

In an embodiment, the linker-payload conjugate is the linker-payload conjugate according to Formula IIIb, Formula IIIc or Formula IIId, wherein D is a cytotoxic drug.

In an embodiment, the linker-payload conjugate comprises the linker-payload conjugate according to Formula IIIb, Formula IIIc or Formula IIId, wherein D is an auristatin. In an embodiment, the linker-payload conjugate is the linker-payload conjugate according to Formula IIIb, Formula IIIc or Formula IIId, wherein D is an auristatin.

In an embodiment, the linker-payload conjugate comprises the linker-payload conjugate according to Formula IIIb, Formula Inc or Formula IIId, wherein D is MMAU. In an embodiment, the linker-payload conjugate is the linker-payload conjugate according to Formula IIIb, Formula IIIc or Formula IIId, wherein D is MMAU.

In an embodiment, the linker-payload conjugate comprises the linker-payload conjugate according to Formula III, Formula IIIb, Formula IIIc or Formula IIId, wherein D is a rubicin or a doxyrubicin derivative. In an embodiment, the linker-payload conjugate is the linker-payload conjugate according to Formula III, Formula IIIb, Formula IIIc or Formula IIId, wherein D is a rubicin or a doxyrubicin derivative.

In an embodiment, the linker-payload conjugate comprises the linker-payload conjugate according to Formula IIIb, Formula Inc or Formula IIId, wherein D is PNU-EDA. In an embodiment, the linker-payload conjugate is the linker-payload conjugate according to Formula III, Formula IIIb, Formula IIIc or Formula IIId, wherein D is PNU-EDA.

In an embodiment, the linker-payload conjugate is DBCO-Val-Ser(GlcA)-PNU-EDA according to Formula Vb Formula Vb

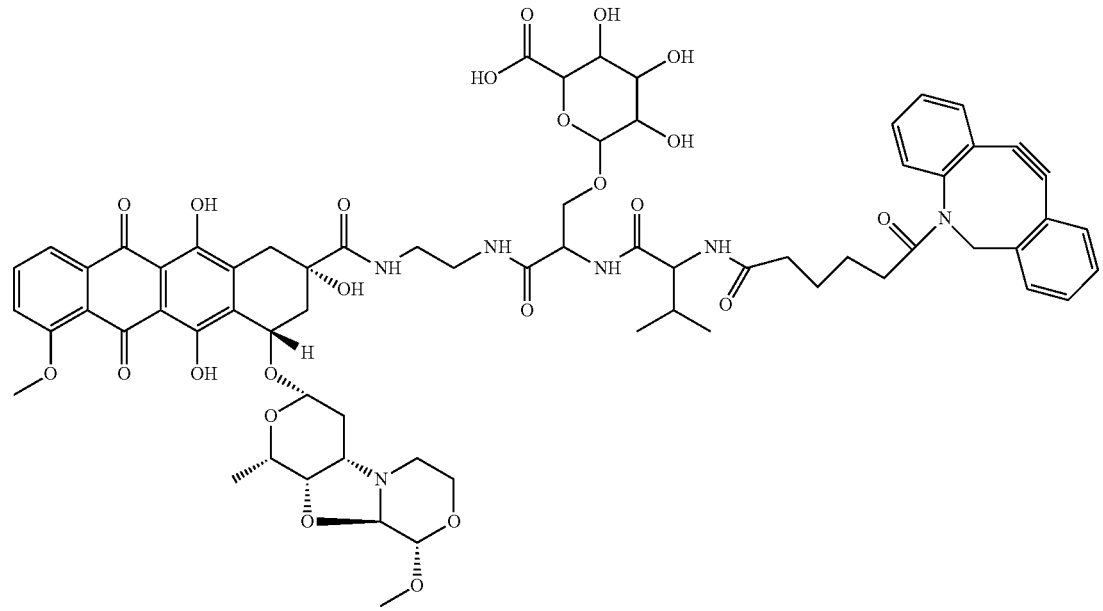

In an embodiment, the targeting unit-linker-payload conjugate comprises the targeting unit-linker-payload conjugate according to Formula IVb, Formula IVc or Formula IVd, wherein D is a cytotoxic drug. In an embodiment, the targeting unit-linker-payload conjugate is the targeting unit-linker-payload conjugate according to Formula IVb, Formula IVc or Formula IVd, wherein D is a cytotoxic drug.

In an embodiment, the targeting unit-linker-payload conjugate comprises the targeting unit-linker-payload conjugate according to Formula IVb, wherein D is an auristatin. In an embodiment, the targeting unit-linker-payload conjugate is the targeting unit-linker-payload conjugate according to Formula IVb, wherein D is an auristatin.

In an embodiment, the targeting unit-linker-payload conjugate comprises the targeting unit-linker-payload conjugate according to Formula IV, Formula IVb, Formula IVc or Formula IVd, wherein D is a rubicin or a doxorubicin derivative. In an embodiment, the targeting unit-linker-payload conjugate is the targeting unit-linker-payload conjugate according to Formula IV, Formula IVb, Formula IVc or Formula IVd, wherein D is a rubicin or a doxorubicin derivative.

In an embodiment, the targeting unit-linker-payload conjugate comprises the targeting unit-linker-payload conjugate according to Formula IVb, wherein D is MMAU. In an embodiment, the targeting unit-linker-payload conjugate is the targeting unit-linker-payload conjugate according to Formula IVb, wherein D is MMAU.

In an embodiment, the targeting unit-linker-payload conjugate comprises the targeting unit-linker-payload conjugate according to Formula IV, Formula IVb, Formula IVc or Formula IVd, wherein D is PNU-EDA. In an embodiment, the targeting unit-linker-payload conjugate is the targeting unit-linker-payload conjugate according to Formula IV, Formula IVb, Formula IVc or Formula IVd, wherein D is PNU-EDA.

In an embodiment, the targeting unit-linker-payload conjugate is antibody-DBCO-Val-Ser(GlcA)-PNU-EDA according to Formula VIb Formula VIb

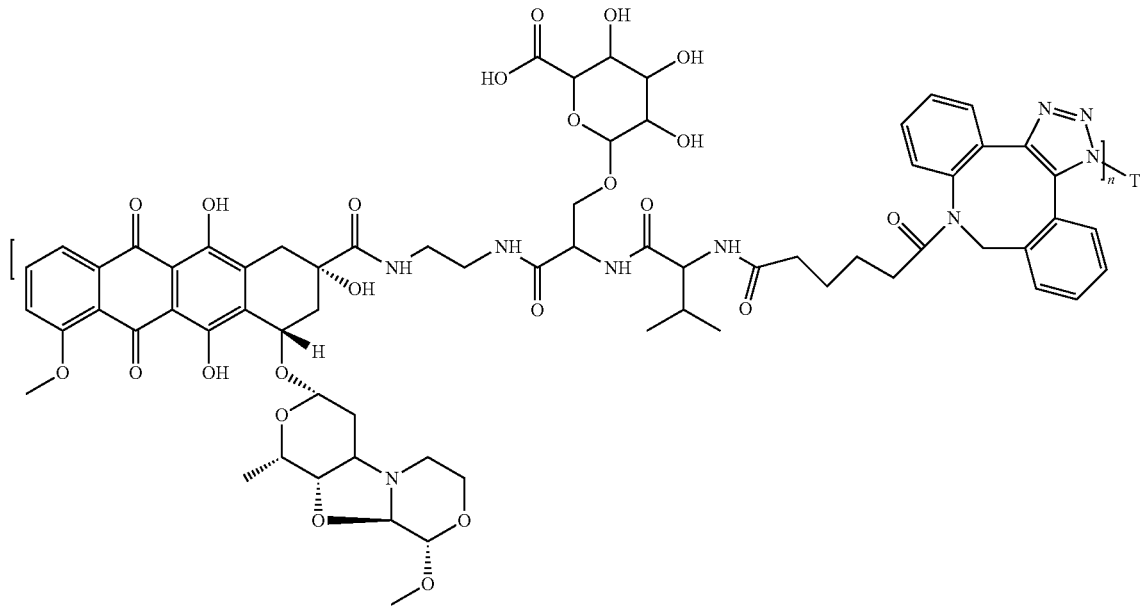

wherein T is an antibody connected from an azide group via a 1,3-triazole and n is between 1 and about 4.

In an embodiment, the targeting unit-linker-payload conjugate comprises or is a targeting unit-linker-payload conjugate according to Formula IVb, Formula IVc or Formula IVd, wherein D is a cytotoxic drug and T is trastuzumab.

In an embodiment, the targeting unit-linker-payload conjugate comprises or is a targeting unit-linker-payload conjugate according to Formula IVb, wherein D is MMAU and T is trastuzumab.

In an embodiment, the targeting unit-linker-payload conjugate comprises or is a targeting unit-linker-payload conjugate according to Formula IV, Formula IVb, Formula IVc or Formula IVd, wherein D is PNU-EDA and T is trastuzumab.

In an embodiment, the targeting unit-linker-payload conjugate comprises or is a conjugate selected from the group consisting of the following:

a targeting unit-linker-payload conjugate according to Formula IVb, Formula IVc or Formula IVd, wherein D is a cytotoxic drug;

a targeting unit-linker-payload conjugate according to Formula IVb, wherein D is an auristatin;

a targeting unit-linker-payload conjugate according to Formula IV, Formula IVb, Formula IVc or Formula IVd, wherein D is a rubicin or a doxorubicin derivative;

a targeting unit-linker-payload conjugate according to Formula IVb, wherein D is MMAU;

a targeting unit-linker-payload conjugate according to Formula IV, Formula IVb, Formula IVc or Formula IVd, wherein D is PNU-EDA.

In an embodiment, the conjugate comprises or is a conjugate selected from the group consisting of the following:

a linker-payload conjugate according to Formula IIIb, Formula IIIc or Formula IIId, wherein D is a cytotoxic drug;

a linker-payload conjugate according to Formula IIIb, wherein D is an auristatin;

a linker-payload conjugate according to Formula III, Formula IIIb, Formula IIIc or Formula IIId, wherein D is a rubicin or a doxorubicin derivative;

a linker-payload conjugate according to Formula IIIb, wherein D is MMAU;

a linker-payload conjugate according to Formula III, Formula IIIb, Formula IIIc or Formula IIId, wherein D is PNU-EDA.

Targeting unit-linker-payload conjugates can be prepared using cross-linking reagents. For example, a cysteine, thiol or an amine, e.g. N-terminus or an amino acid side chain, such as lysine of the antibody, can form a bond with a functional group of a cross-linking reagent.

The linkers according to the present invention can be prepared by standard methods known to a person skilled in the art. For example, the central amino acid and peptide groups of the linker can be prepared by standard peptide chemistry and automated peptide chemistry, and ordered from a commercial manufacturer of synthetic peptides; and the saccharide, sulfate, phosphate, phosphodiester and phosphonate group Y can be added to the amino acid and peptide groups during or after their synthesis from commercially available protected building blocks. Further, the self-immolative group Z and spacer group X can be added to the amino acid and peptide groups by standard chemistry forming amide bonds to the amino acid and peptide groups.

General methods to prepare the targeting unit-payload conjugates, i.e. addition of the payload D and the targeting unit T, are known for the skilled artisan, and for example, described in WO/2016/001485, WO/2014/096551 and WO/2014/177771.

The targeting unit-linker-payload conjugates and linker-payload conjugates can be characterized and selected for their physical/chemical properties and/or biological activities by various assays known in the art.

For example, a conjugate can be tested for its antigen binding activity by known methods such as ELISA, FACS, Biacore or Western blot.

Transgenic animals and cell lines are particularly useful in screening conjugates that have potential as prophylactic or therapeutic treatments of cancer of tumor-associated antigens and cell surface receptors. Screening for a useful conjugate may involve administering a candidate conjugate over a range of doses to the transgenic animal, and assaying at various time points for the effect(s) of the conjugate on the disease or disorder being evaluated. Alternatively, or additionally, the drug can be administered prior to or simultaneously with exposure to an inducer of the disease, if applicable. The candidate conjugate may be screened serially and individually, or in parallel under medium or high-throughput screening format.

A method for preparing the targeting unit-linker-payload conjugate according to one or more embodiments is disclosed, comprising conjugating the linker-payload according to one or more embodiments to a targeting unit, optionally via a spacer group.

Many ways of conjugating payload molecules to targeting units, for example, antibodies are known, and in principle any way that is suitable for conjugating a payload to a targeting unit may be used. The linker-payload according to one or more embodiments may be conjugated to the targeting unit such as an antibody directly or indirectly, for instance via a spacer group. In an embodiment, the linker-payload according to one or more embodiments and comprising a maleimide is conjugated to the antibody by reducing hinge region cystines with a reducing agent and contacting the reduced antibody with the linker-payload to form thioether bond.

In this context, the antibody may in principle be any antibody, and in particular any antibody described in this specification.

In an embodiment, the linker-payload conjugate is according to Formula III

Formula III

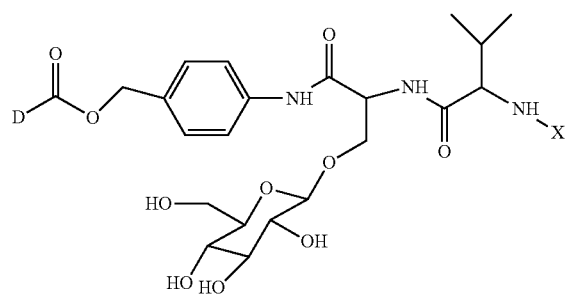

wherein X is a spacer group comprising a maleimide and D is a payload molecule.

In an embodiment, the antibody-linker-payload conjugate is according to Formula

Formula IV

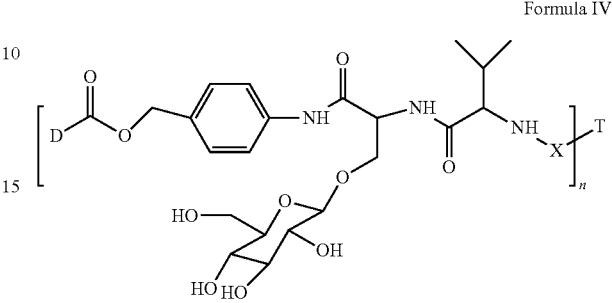

wherein T is an antibody, n is between 1 and about 20, X is a spacer group comprising a maleimide connected to a cysteine side chain of the antibody via a thioether bond and D is a payload molecule.

In an embodiment, the linker-payload conjugate comprises the linker-payload conjugate according to Formula III, wherein D is a cytotoxic drug. In an embodiment, the linker-payload conjugate is the linker-payload conjugate according to Formula III, wherein D is a cytotoxic drug.

In an embodiment, the linker-payload conjugate comprises the linker-payload conjugate according to Formula III, wherein D is an auristatin. In an embodiment, the linker-payload conjugate is the linker-payload conjugate according to Formula III, wherein D is an auristatin.

In an embodiment, the linker-payload conjugate comprises the linker-payload conjugate according to Formula III, wherein D is MMAU. In an embodiment, the linker-payload conjugate is the linker-payload conjugate according to Formula III, wherein D is MMAU.

In an embodiment, the linker-payload conjugate is maleimidocaproyl-Val-Ser(Glc)-PABC-MMAU according to Formula V Formula V

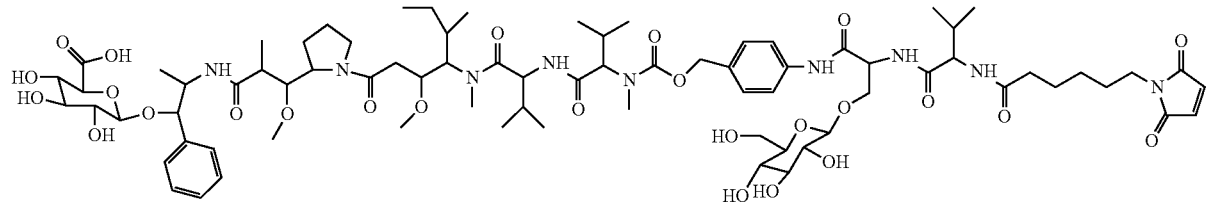

In an embodiment, the targeting unit-linker-payload conjugate comprises the targeting unit-linker-payload conjugate according to Formula IV, wherein D is a cytotoxic drug.

In an embodiment, the targeting unit-linker-payload conjugate is the targeting unit-linker-payload conjugate according to Formula IV, wherein D is a cytotoxic drug.

In an embodiment, the targeting unit-linker-payload conjugate comprises the targeting unit-linker-payload conjugate according to Formula IV, wherein D is an auristatin. In an embodiment, the targeting unit-linker-payload conjugate is the targeting unit-linker-payload conjugate according to Formula IV, wherein D is an auristatin.

In an embodiment, the targeting unit-linker-payload conjugate comprises the targeting unit-linker-payload conjugate according to Formula IV, wherein D is MMAU. In an embodiment, the targeting unit-linker-payload conjugate is the targeting unit-linker-payload conjugate according to Formula IV, wherein D is MMAU.

In an embodiment, the targeting unit-linker-payload conjugate is antibody-maleimidocaproyl-Val-Ser(Glc)-PABC-MMAU according to Formula VI In an embodiment, the targeting unit-linker-payload conjugate is antibody-maleimidocaproyl-Val-Ser(Glc)-PABC-MMAU according to Formula VI, wherein T is trastuzumab connected from a cysteine side chain via a thioether bond and n is 7.

In an embodiment, the targeting unit-linker-payload conjugate is antibody-maleimidocaproyl-Val-Ser(Glc)-PABC-MMAU according to Formula VI, wherein T is trastuzumab connected from a cysteine side chain via a thioether bond and n is 8.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4. In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, n is 5.
In an embodiment, n is 6.

Formula VI

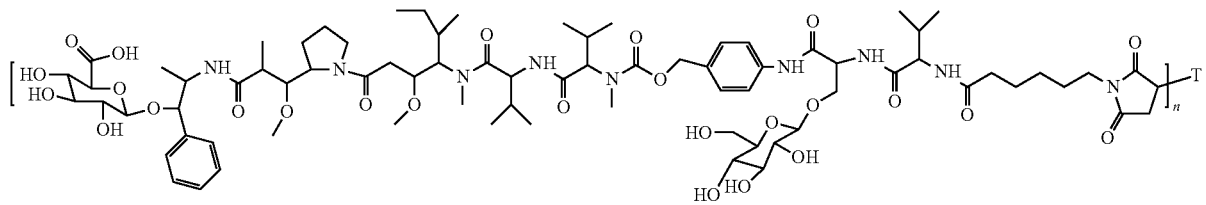

wherein T is an antibody connected from a cysteine side chain via a thioether bond and n is between 1 and about 20.

In an embodiment, the targeting unit-linker-payload conjugate is antibody-maleimidocaproyl-Val-Ser(Glc)-PABC-MMAU according to Formula VI, wherein T is an antibody connected from a cysteine side chain via a thioether bond and n is 5.

In an embodiment, the targeting unit-linker-payload conjugate is antibody-maleimidocaproyl-Val-Ser(Glc)-PABC-MMAU according to Formula VI, wherein T is an antibody connected from a cysteine side chain via a thioether bond and n is 6.

In an embodiment, the targeting unit-linker-payload conjugate is antibody-maleimidocaproyl-Val-Ser(Glc)-PABC-MMAU according to Formula VI, wherein T is an antibody connected from a cysteine side chain via a thioether bond and n is 7.

In an embodiment, the targeting unit-linker-payload conjugate is antibody-maleimidocaproyl-Val-Ser(Glc)-PABC-MMAU according to Formula VI, wherein T is an antibody connected from a cysteine side chain via a thioether bond and n is 8.

In an embodiment, the targeting unit-linker-payload conjugate is antibody-maleimidocaproyl-Val-Ser(Glc)-PABC-MMAU according to Formula VI, wherein T is trastuzumab connected from a cysteine side chain via a thioether bond and n is 5.

In an embodiment, the targeting unit-linker-payload conjugate is antibody-maleimidocaproyl-Val-Ser(Glc)-PABC-MMAU according to Formula VI, wherein T is trastuzumab connected from a cysteine side chain via a thioether bond and n is 6.

In an embodiment, n is 7.
In an embodiment, n is 8.
In an embodiment, n is 9.

In an embodiment, the antibody is selected from the group of an anti-EGFR1 antibody, cetuximab, imgatuximab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the targeting unit-linker-payload conjugate comprises or is a targeting unit-linker-payload conjugate according to Formula IV, wherein D is a cytotoxic drug and T is trastuzumab.

In an embodiment, the targeting unit-linker-payload conjugate comprises or is a targeting unit-linker-payload conjugate according to Formula IV, wherein D is MMAU and T is trastuzumab.

In an embodiment, the targeting unit-linker-payload conjugate comprises or is a conjugate selected from the group consisting of the following:

a targeting unit-linker-payload conjugate according to Formula IV, wherein D is a cytotoxic drug;

a targeting unit-linker-payload conjugate according to Formula IV, wherein D is an auristatin;

a targeting unit-linker-payload conjugate according to Formula IV, wherein D is MMAU.

In an embodiment, the conjugate comprises or is a conjugate selected from the group consisting of the following:

a linker-payload conjugate according to Formula III, wherein D is a cytotoxic drug;

a linker-payload conjugate according to Formula III, wherein D is an auristatin;

a linker-payload conjugate according to Formula III, wherein D is MMAU.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4.

In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, n is 5.

In an embodiment, n is 6.

In an embodiment, n is 7.

In an embodiment, n is 8.

In an embodiment, n is 9.

A pharmaceutical composition comprising the linker-payload conjugate according to one or more embodiments or the targeting unit-linker-payload conjugate according to one or more embodiments is disclosed.

The pharmaceutical composition may further comprise a pharmaceutically acceptable carrier. Examples of suitable pharmaceutically acceptable carriers are well known in the art and may include e.g. phosphate buffered saline solutions, water, oil/water emulsions, wetting agents, and liposomes. Compositions comprising such carriers may be formulated by methods well known in the art. The pharmaceutical composition may further comprise other components such as vehicles, additives, preservatives, other pharmaceutical compositions administrated concurrently, and the like.

In an embodiment, the pharmaceutical composition comprises an effective amount of the linker-payload conjugate according to one or more embodiments.

In an embodiment, the pharmaceutical composition comprises an effective amount of the targeting unit-linker-payload conjugate according to one or more embodiments.

In an embodiment, the pharmaceutical composition comprises a therapeutically effective amount of the linker-payload conjugate according to one or more embodiments.

In an embodiment, the pharmaceutical composition comprises a therapeutically effective amount of the targeting unit-linker-payload conjugate according to one or more embodiments.

The term "therapeutically effective amount" or "effective amount" of the targeting unit-linker-payload conjugate should be understood as referring to the dosage regimen for modulating the growth of cancer cells and/or treating a patient's disease. The therapeutically effective amount can also be determined by reference to standard medical texts, such as the Physicians Desk Reference 2004. The patient may be male or female, and may be an infant, child or adult.

The term "treatment" or "treat" is used in the conventional sense and means attending to, caring for and nursing a patient with the aim of combating, reducing, attenuating or alleviating an illness or health abnormality and improving the living conditions impaired by this illness, such as, for example, with a cancer disease.

In an embodiment, the pharmaceutical composition comprises a composition for e.g. oral, parenteral, transdermal, intraluminal, intraarterial, intrathecal and/or intranasal administration or for direct injection into tissue. Administration of the pharmaceutical composition may be effected in different ways, e.g. by intravenous, intraperitoneal, subcutaneous, intramuscular, intratumoral, topical or intradermal administration.

A targeting unit-linker-payload conjugate according to one or more embodiments or the pharmaceutical composition according to one or more embodiments for use as a medicament is disclosed.

A linker-payload conjugate according to one or more embodiments for use as a medicament is disclosed.

A targeting unit-linker-payload conjugate according to one or more embodiments or the pharmaceutical composition according to one or more embodiments for use in the treatment of cancer is disclosed.

A linker-payload conjugate according to one or more embodiments for use in the treatment of cancer is disclosed.

In an embodiment, the cancer is selected from the group consisting of leukemia, lymphoma, breast cancer, prostate cancer, ovarian cancer, colorectal cancer, gastric cancer, squamous cancer, small-cell lung cancer, head-and-neck cancer, multidrug resistant cancer, glioma, melanoma and testicular cancer.

A method of treating and/or modulating the growth of and/or prophylaxis of tumor cells in humans or animals is disclosed, wherein the linker-payload conjugate according to one or more embodiments, targeting unit-linker-payload conjugate according to one or more embodiments or the pharmaceutical composition according to one or more embodiments is administered to a human or animal in an effective amount.

In an embodiment, the tumor cells are selected from the group consisting of leukemia cells, lymphoma cells, breast cancer cells, prostate cancer cells, ovarian cancer cells, colorectal cancer cells, gastric cancer cells, squamous cancer cells, small-cell lung cancer cells, head-and-neck cancer cells, multidrug resistant cancer cells, and testicular cancer cells.

A method of treating cancer in humans is disclosed, wherein the linker-payload conjugate according to one or more embodiments, the targeting unit-linker-payload conjugate according to one or more embodiments or the pharmaceutical composition according to one or more embodiments is administered to a human in an effective amount.

In an embodiment, the effective amount is a therapeutically effective amount.

In an embodiment, the linker-payload conjugate according to one or more embodiments, the targeting unit-linker-payload conjugate according to one or more embodiments or the pharmaceutical composition according to one or more embodiments is administered intravenously to a human in a therapeutically effective amount.

In an embodiment, the linker-payload conjugate according to one or more embodiments, the targeting unit-linker-payload conjugate according to one or more embodiments or the pharmaceutical composition according to one or more embodiments is administered intratumorally to a human in a therapeutically effective amount.

In an embodiment, the cancer is selected from the group consisting of head-and-neck cancer, leukemia, lymphoma, breast cancer, prostate cancer, ovarian cancer, colorectal cancer, gastric cancer, squamous cancer, small-cell lung cancer, multidrug resistant cancer and testicular cancer.

The embodiments of the invention described hereinbefore may be used in any combination with each other. Several of the embodiments may be combined together to form a further embodiment of the invention. A product or a method to which the invention is related may comprise at least one of the embodiments of the invention described hereinbefore.

The linker-payload conjugate according to one or more embodiments and the targeting unit-linker-payload conjugate according to one or more embodiments may have a number of advantageous properties.

The presence of the cleavable hydrophilic group renders the otherwise relatively poorly water-soluble linker more soluble in aqueous and physiological solutions. The improved solubility also improves the retention of the targeting unit-linker-payload conjugate in serum. It may also have high uptake in cells to which it is targeted and low uptake in cells and organs to which it is not targeted.

The targeting unit-linker-payload conjugate according to one or more embodiments is less toxic in the absence or low activity of lysosomal and intracellular enzymes. Since cancer cells typically display high activity of lysosomal and/or intracellular enzymes, the toxic payload moiety is preferentially released in cancer cells as compared to non-cancer cells.

The conjugate has low antigenicity.

The targeting unit-linker-payload conjugate according to one or more embodiments also exhibits good pharmacokinetics. It has suitable retention in blood, high uptake in cells to which it is targeted and low uptake in cells and organs to which it is not targeted.

The targeting unit-linker-payload conjugate according to one or more embodiments is sufficiently stable towards chemical or biochemical degradation during manufacturing or in physiological conditions, e.g. in blood, serum, plasma or tissues.

EXAMPLES

In the following, the present invention will be described in more detail. Reference will now be made in detail to the embodiments, examples of which are illustrated in the accompanying drawings. The description below discloses some embodiments in such detail that a person skilled in the art is able to utilize the invention based on the disclosure. Not all steps of the embodiments are discussed in detail, as many of the steps will be obvious for the person skilled in the art based on this specification.

Example 1. Synthesis of Fmoc-Val-Ser(GlcOAc$_4$)-PABC-(β-D-Glucuronyl)-Monomethylauristatin E (MMAU)

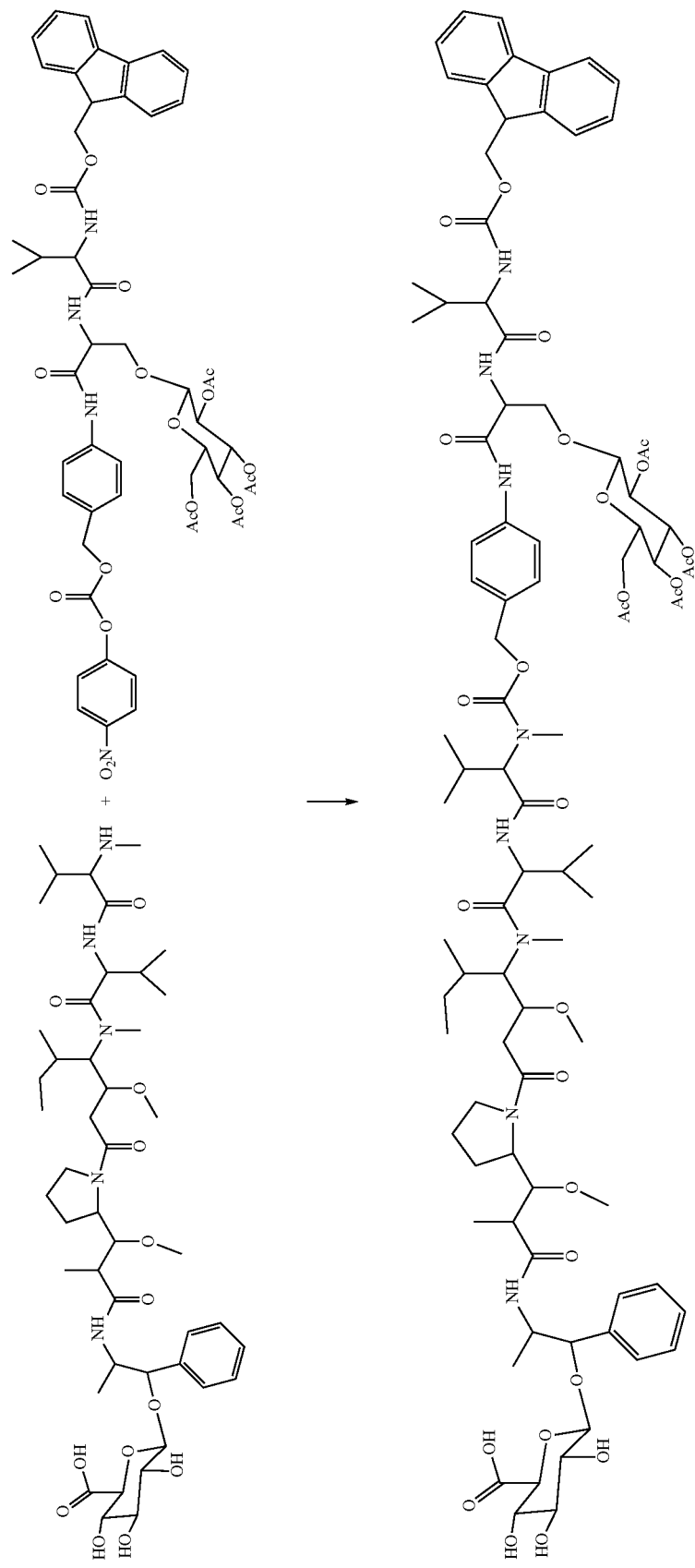
Scheme 1. Synthesis of Fmoc-Val-Ser(GlcOAc4)-PABC-MMAU.

2.4 mg (2.8 µmop β-D-glucuronyl-monomethylauristatin E (MMAU; Concortis, USA) in dimethylformamide (DMF; 100 µl), 1.9 molar excess of Fmoc-Val-Ser(GlcOAc$_4$)-PABC-paranitrophenyl, 3 µl 0.5 M (1.5 µmop HOBt and 12 µl (68 µmop diisopropylethylamine (DIPEA) were stirred overnight at room temperature. Fmoc-Val-Ser(GlcOAc$_4$)-PABC-MMAU was purified by HPLC with C18 reverse phase column. MALDI-TOF mass spectrometric analysis of the product fraction showed the expected mass (m/z 1803, [M+Na]$^+$).

Example 2. Synthesis of Maleimidocaproyl-Val-Ser (Glc)-PABC-(β-Glucuronyl)-Monomethylauristatin E Scheme 2. Maleimidocaproyl-Val-Ser(Glc)-PABC-MMAU.

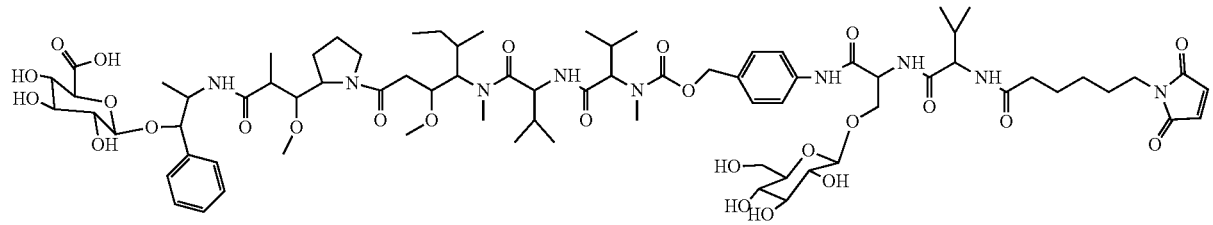

After removing the Fmoc and acetyl protecting groups from Fmoc-Val-Ser(GlcOAc$_4$)-PABC-MMAU, 600 nmol of the resulting Val-Ser(Glc)-PABC-MMAU was reacted overnight at room temperature with 3 µmol of EMCS (N-ε-malemidocaproyl-oxysuccinimide ester, Thermo Fisher) in the presence of DIPEA in DMF. The successfully prepared and HPLC-purified product was analyzed with matrix-assisted laser desorption-ionization time-of-flight (MALDI-TOF) mass spectrometry, showing the expected mass at m/z 1606.955 for the [M+Na]$^+$ ion as well as at m/z 1628.979 for the [M-H+2Na]$^+$ (FIG. 1).

Example 3. Preparation of Trastuzumab-Linker-MMAU Conjugate 0.5 mg of trastuzumab (Herceptin; Roche) in phosphate-buffered saline (PBS) was reduced in the presence of 50 nmol of DTPA and 67 nmol of TCEP at +37 C for 1.5 hours, after which the reagents were removed and buffer exchanged into PBS containing 5% mannitol, 0.1% Tween, 1 mM DTPA, propylene glycol, DMSO and 69 nmol of maleimidocaproyl-Val-Ser(Glc)-PABC-MMAU. After 1 hour's reaction at room temperature, the reagents were removed and buffer exchanged into PBS containing 5% mannitol and 0.1% Tween. The antibody-drug conjugate was analyzed by MALDI-TOF mass spectrometric analysis after digestion with FabRICATOR enzyme (Genovis, Sweden) and microscale purification of the resulting antibody fragments with Poros R$_1$ material (FIG. 2). The analysis showed that the prepared trastuzumab-maleimidocaproyl-Val-Ser(Glc)-PABC-MMAU conjugate had a drug-to-antibody ratio of about 8 (DAR=7.8).

Example 4. HIC HPLC of Trastuzumab-Linker-MMAU Conjugate

HIC HPLC chromatography on a Butyl-NPR column was performed to the DAR=7.8 trastuzumab-maleimidocaproyl-Val-Ser(Glc)-PABC-MMAU as well as the naked antibody trastuzumab and DAR=8 maleimidocaproyl-Val-Cit-PAB-MMAU prepared using standard Val-Cit linker. The gradient was from 100% buffer A (1.5 M ammonium sulfate in 25 mM potassium phosphate buffer pH 7) to 90% buffer A/10% buffer B (25% isopropanol in 25 mM potassium phosphate buffer pH 7) in 15 minutes with a flow rate of 1 ml/min. The elution position of DAR=7.8 trastuzumab-maleimidocaproyl-Val-Ser(Glc)-PABC-MMAU was at 6.2 minutes compared to trastuzumab at 5.3 minutes and DAR=8 maleimidocaproyl-Val-Cit-PABC-MMAU at 8.8 minutes, demonstrating markedly increased hydrophilicity (near the naked antibody) of DAR=7.8 trastuzumab-maleimidocaproyl-Val-Ser(Glc)-PABC-MMAU compared to DAR=8 trastuzumab-maleimidocaproyl-Val-Cit-PABC-MMAU prepared using standard Val-Cit linker (FIG. 3).

Scheme 3. Trastuzumab-maleimidocaproyl-Val-Ser(Glc)-PABC-MMAU; T is trastuzumab and n is about 8.

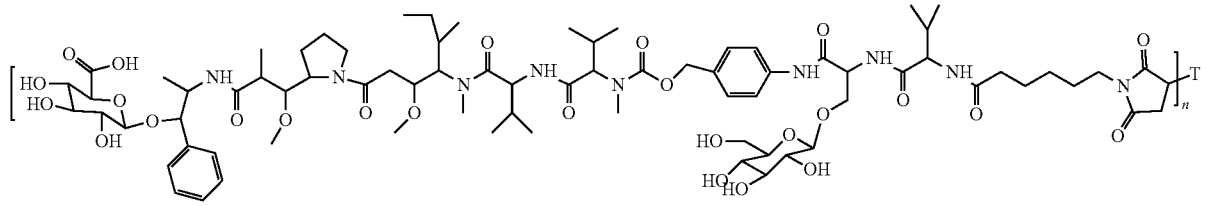

Example 5. Cytotoxicity Assay of Trastuzumab-Linker-MMAU Conjugates

Cytotoxicity of trastuzumab-maleimidocaproyl-Val-Ser (Glc)-PABC-MMAU conjugate (DAR=7.8) and trastuzumab-maleimidocaproyl-Val-Cit-PABC-MMAU conjugate (DAR=8) towards HER2+ SKOV-3 ovarian cancer cells was evaluated by incubating a serial dilution series of each conjugate with the cells for four days and evaluating the viability with PrestoBlue reagent. Both ADCs had cytotoxicity with IC50 below 100 pM, showing that the trastuzumab-maleimidocaproyl-Val-Ser(Glc)-PABC-MMAU conjugate was highly active as an ADC and that the linker was effectively cleaved inside the cancer cells (FIG. 4).

Example 6. Pharmacokinetics in Mice

Healthy Envigo HSD:Athymic nude Foxnlnu mice were given a single i.v. dose of 10 mg/kg of either trastuzumab (Roche), trastuzumab-maleimidocaproyl-Val-Cit-PABC-MMAE conjugate (DAR=8) or trastuzumab-maleimidocaproyl-Val-Ser(Glc)-PABC-MMAU conjugate (DAR=8), four mice in each study group. The conjugates were prepared as described in the previous Examples. Serum samples were collected before the injection and 5 min, 1 d, 4 d, 7 d, 11 d and 15 d after the injection. Human IgG (ADC) were measured in each sample by ELISA assay (Human IgG quantification kit, RD-Biotech). The results are shown in FIG. 5 and in the Table below. Whereas the trastuzumab-maleimidocaproyl-Val-Cit-PABC-MMAE conjugate (DAR=8) was rapidly lost from circulation, the trastuzumab-maleimidocaproyl-Val-Ser(Glc)-PABC-MMAU conjugate (DAR=8) was retained in circulation at comparable levels to trastuzumab, thus showing that the Val-Ser(Glc) linker had improved the biocompatibility, pharmacokinetics and systemic exposure of the ADC.

| Time point h | T-mc-vs(G)-MMAU DAR = 8 µg/mL | SEM | % | T-vc-MMAE DAR = 8 µg/mL | SEM | % | Trastuzumab µg/mL | SEM | % |
|---|---|---|---|---|---|---|---|---|---|
| 0 | 0.09 | | | 0.06 | | | 0.02 | | |
| 0.08 | 108.03 | 7.34 | 100.0 | 138.52 | 17.95 | 100.0 | 143.41 | 3.66 | 100.0 |
| 24 | 38.61 | 1.91 | 35.7 | 46.03 | 6.06 | 33.2 | 61.27 | 5.11 | 42.7 |
| 96 | 24.49 | 4.46 | 22.7 | 6.77 | 0.25 | 4.9 | 45.00 | 5.68 | 31.4 |
| 168 | 17.03 | 3.56 | 15.8 | 4.56 | 0.71 | 3.3 | 38.47 | 6.69 | 26.8 |
| 264 | 13.67 | 4.21 | 12.7 | 1.90 | 0.65 | 1.4 | 23.02 | 3.82 | 16.0 |
| 360 | 9.90 | 3.27 | 9.2 | 1.09 | 0.35 | 0.8 | 17.26 | 3.08 | 12.0 |

Example 7. Mechanism of Linker Cleavage

Acylated Val-Ser(Glc)-PABC-MMAU linker-drug compound was prepared as described in the previous Examples. To study its susceptibility to cleavage with lysosomal enzyme activities, it was incubated with recombinant human cathepsin B (R&D Systems) with or without a recombinant β-glucosidase enzyme. The reactions were carried out in 50 mM sodium acetate buffer pH 5.5 at +37° C. overnight after activation of the cathepsin with 5 mM dithiotreitol in 50 mM sodium acetate buffer pH 5.5. The reaction was followed by MALDI-TOF mass spectrometry. Cathepsin B without β-glucosidase did not cleave the linker-drug compound, although it cleaved maleimidocaproyl-Val-Cit-PABC-MMAU liberating free MMAU as detected by mass spectrometry. The β-glucosidase alone cleaved the β-glucose residue from the linker-drug compound, transforming it into a deglucosylated product at 162 Da less mass. Cathepsin B with the β-glucosidase cleaved the linker-drug compound, liberating free MMAU drug at m/z 916.8 and 938.8 for sodium adduct ion as expected. Thus, it was demonstrated that the glycoside efficiently protected the linker from cathepsin B-induced cleavage and that after β-glucosidase digestion the peptide was cleavable by cathepsin and liberated the free drug from the self-immolative group. Trastuzumab ADCs with DAR=8 were prepared as described in the previous Examples. In vitro cytotoxicity assay with SKOV-3 cells, performed as described in the previous Examples, showed that the Val-Ser(Glc) linker was cleaved as efficiently (IC50=73 pM) as the Val-Cit linker (IC50=80 pM) in target cells after ADC internalization (FIG. 6).

Example 8. Preparation of Trastuzumab-Linker-PNU-EDA Conjugate

Scheme 4. Trastuzumab-Val-Ser(GlcA)-PNU-EDA; T is trastuzumab and n is 2.

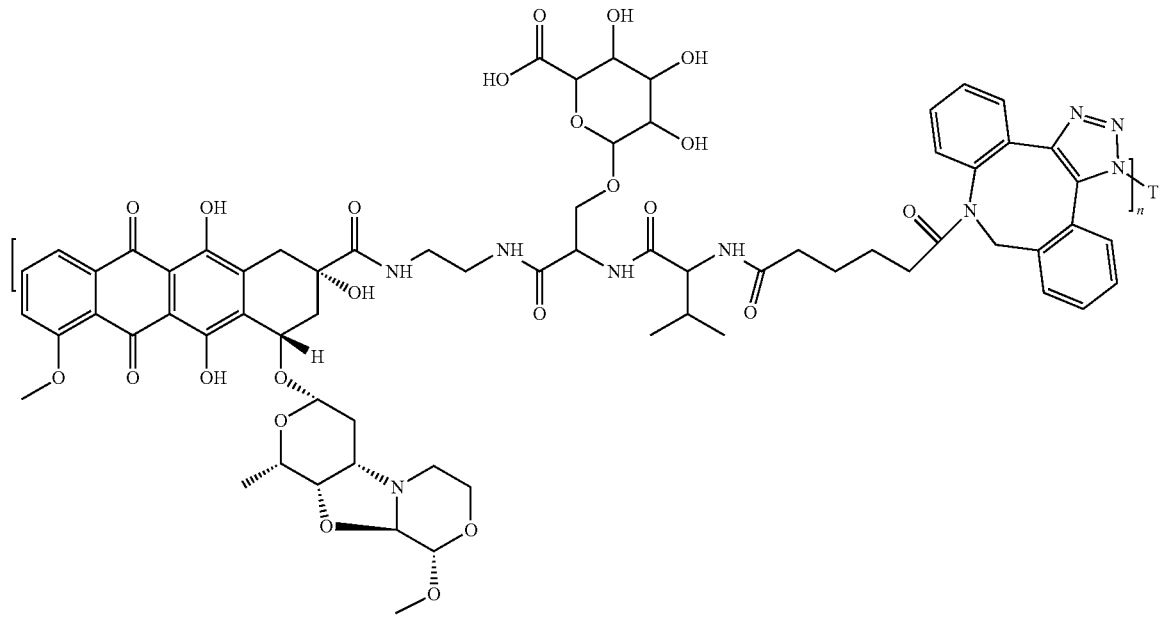

4 mg of anti-HER2 antibody Trastuzumab (Herceptin, Roche) was digested with endoglycosidase S2 according to manufacturers instructions (Glycinator; Genovis, Lund, Sweden) and then incubated with 0.4 mg recombinant Y289L mutant bovine β1,4-galactosyltransferase and 1.3 mg UDP-GaNAz (both from Thermo, Eugene, USA) in the presence of $Mn^{2+}$ containing buffer at +37° C. overnight. Azide-to-antibody ratio was determined by Fabricator enzyme digestion according to manufacturer's instructions (Genovis) and MALDI-TOF MS essentially as described (Satomaa et al. 2018. Antibodies 7(2), 15), demonstrating that the azide-to-antibody ratio was 2. Unreacted UDP-GaNAz was removed by repeated concentration in Amicon centrifugal filters with MW 10 kDa cutoff and addition of phosphate-buffered saline, after which 8×mol:mol excess of DBCO-Val-Ser(GlcA)-PNU-EDA was added. The reaction proceeded at room temperature for over an hour, after which unreacted DBCO-Val-Ser(GlcA)-PNU-EDA was removed by repeated concentration in Amicon centrifugal filters with MW 10 kDa cutoff and addition of phosphate-buffered saline. Drug-to-antibody ratio (DAR) was determined by Fabricator enzyme digestion and MALDI-TOF MS as above: heavy chain Fc fragments were detected at m/z 25737.6, consistent with successfully conjugated ADC, and no unreacted heavy chain Fc fragments were detected, demonstrating DAR=2. In contrast, parallel conjugation of the azido-trastuzumab with 8×mol:mol excess of DBCO-Val-Cit-PABC-PNU-EDA, which is a more hydrophobic linker-payload molecule, were only partially successful with precipitation (observed as a slightly cloudy reaction solution) of the linker-payload in the PBS reaction solution and only partial conjugation yielding both unconjugated and conjugated heavy chain Fc fragments in about equal amounts as evidenced by Fabricator/MALDI-TOF MS analysis as above.

Example 9. Cytotoxicity of Trastuzumab-Linker-PNU-EDA Conjugate

Cytotoxicity of 1) DAR=2 trastuzumab-Val-Ser(GlcA)-PNU-EDA towards HER2+ SKOV-3 ovarian cancer cells was evaluated by incubating a serial dilution series of the conjugate with the cells for three days and evaluating the viability with PrestoBlue reagent as above. The ADC had cytotoxicity with IC50 of about 0.01 M (see below), showing that it was highly active as an ADC and that the linker was effectively cleaved inside the cancer cells.

| ADC concentration | Viability of SKOV3 cells (% of control) |
|---|---|
| 3 pM | 99.9 |
| 10 pM | 104.0 |
| 30 pM | 97.2 |
| 100 pM | 62.0 |
| 300 pM | 40.8 |
| 1 nM | 24.6 |
| 3 nM | 18.6 |
| 10 nM | 6.9 |
| 30 nM | 3.1 |
| 100 nM | 23.9 |

Example 10. In Vivo Efficacy of Trastuzumab-Linker-MMAU Conjugate in Tumor Xenograft Mice Seventy five (75) NU(NCr)-Foxnlnu nude mice (9-10 weeks old) were obtained from the Harlan Laboratories and went through 1-week acclimatization per IACUC guidelines (IACUC study LC03337 protocol approval on Jan. 29, 2018; Altogen Labs, Austin, Tex., USA). Mice were housed at Altogen Labs animal facility. The purpose of the study was to test in vivo efficacy of anti-HER2 antibody-drug conjugates (ADCs) compared to control treatment in a subcutaneous HER2-positive tumor xenograft mouse model (NCI-N87 cells, inoculated 1 million cells/mouse in 0.1 ml PBS mixed 1:1 with Matrigel). Trastuzumab-based ADCs conjugated at DAR=8 with maleimidocaproyl-Val-Ser(Glc)-PABC-MMAU were prepared and characterized as described above. Tumors were allowed to grow to approximately 100-150 cubic mm, after which the mice were randomly divided into groups of five mice/group with similar initial tumor sizes between the groups. Treatments were given IV four times at seven day intervals (i.e. once weekly for four weeks). Unconjugated antibody (trastuzumab, positive control) and PBS (negative control) were used in this study as control treatments. Tumor volume data were recorded twice a week. Each animal was evaluated individually and euthanized at the end of the study. Clinical signs and general behavior of the animals is observed in connection with dosing and sampling. Any unusual signs or behavior were recorded. At the end of the study, tumors were prepared and weighed. The tumors were largest in the negative control group (PBS) and the smallest in the DAR=8 trastuzumab-maleimidocaproyl-Val-Ser(Glc)-PABC-MMAU (DAR=8 ADC) group, showing that the ADC had effectively inhibited tumor growth in vivo and that it had increased efficacy compared to the naked antibody treatment (Trastuzumab; see below).

| Treatment | Average tumor size at end of study (mm³) |
|---|---|
| Control (PBS) | 1187 |
| Trastuzumab | 731 |
| DAR = 8 ADC | 477 |

The invention claimed is:

1. A linker-payload conjugate according to:

Formula III

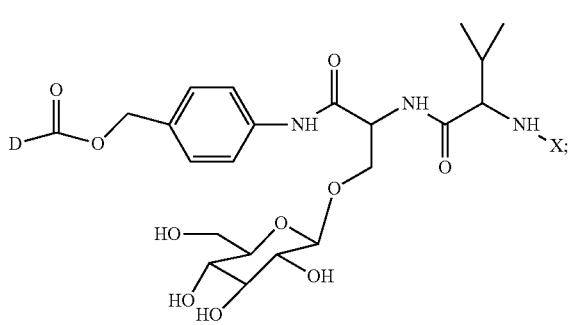

Formula IIIb

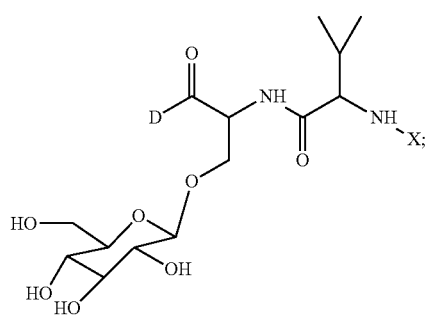

Formula IIIc

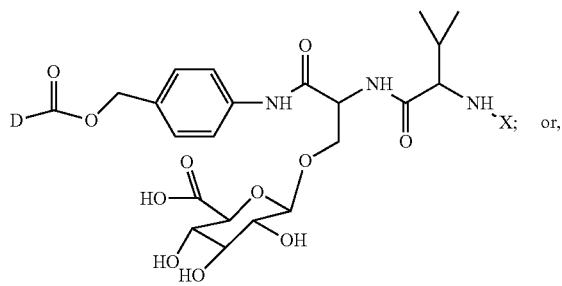

Formula IIId

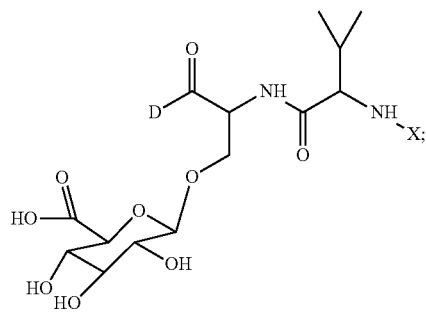

wherein:
X is a spacer group selected from the group consisting of maleimidopropionate, maleimidohexanoate and maleimidocaproyl; and
D is a payload molecule selected from the group consisting of monomethylauristatin E β-D-glucuronide (IV-NIAU), an auristatin, a rubicin, and (PNU-EDA)

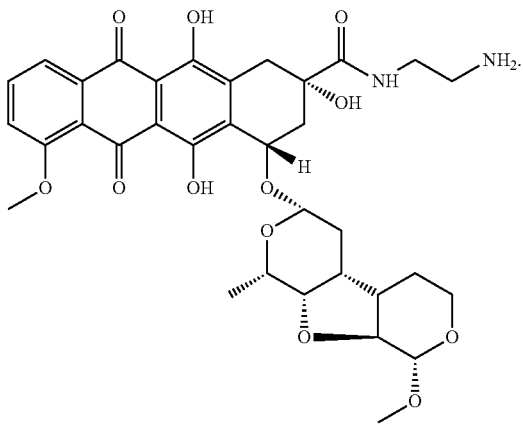

2. A targeting unit-linker-payload conjugate according to:

Formula IV

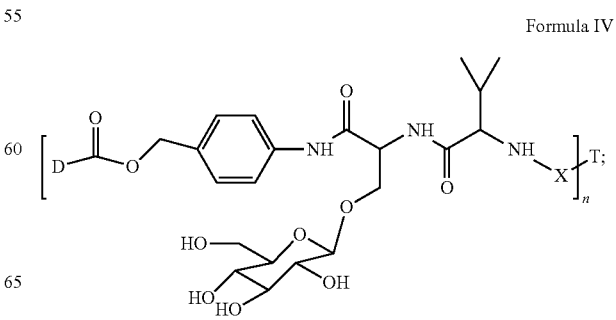

-continued

Formula IVb

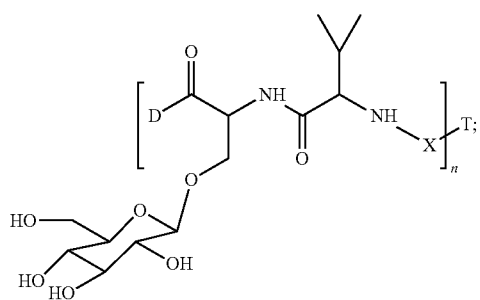

Formula IVc

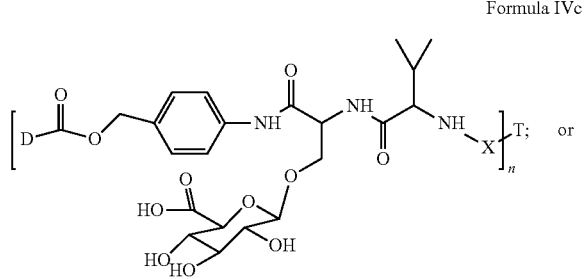

Formula IVd

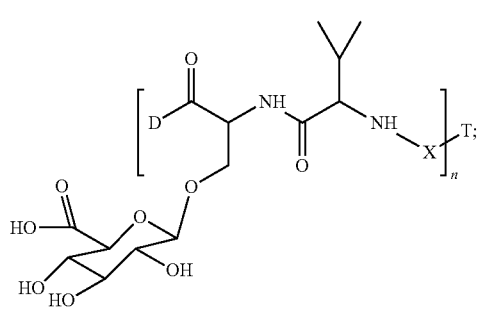

wherein:

T is an antibody and n is between 1 and 20;

X is a spacer group selected from the group consisting of maleimidopropionate, maleimidohexanoate and maleimidocaproyl; and, D is a payload molecule selected from the group consisting of monomethylauristatin E β-D-glucuronide (MMAU), an auristatin, a rubicin, and (PNU-EDA)

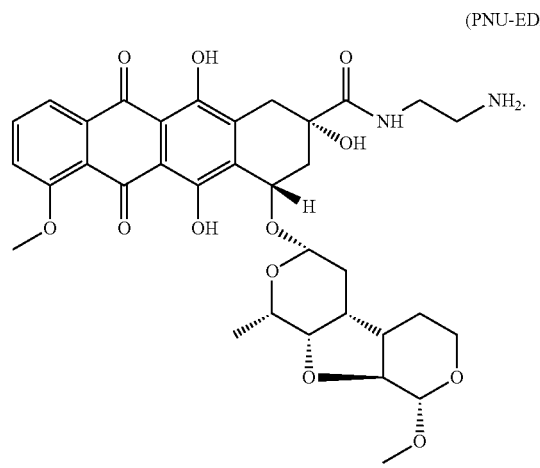

3. The linker-payload conjugate of Formula III of claim 1 wherein D is selected from the group consisting of an auristatin, a rubicin, and MMAU.

4. A linker-paylod conjugate of claim 1 that is maleimidocaproyl-Val-Ser(G1c)-para-aminobenzyloxycarbonyl (PABC)-MMAU.

5. The linker-payload conjugate of claim 1 selected from the group consisting of a linker-payload conjugate of Formula IIIb, Formula IIIc and Formula IIId.

6. The targeting unit-linker-payload conjugate of claim 2 wherein T is trastuzumab.

7. The targeting unit-linker-payload conjugate of claim 2 wherein D is a rubicin.

8. The targeting unit-linker-payload conjugate of claim 2 wherein D is PNU-EDA.

9. The targeting unit-linker-payload conjugate of claim 2 wherein D is PNU-EDA and T is trastuzumab.

10. The targeting unit-linker-payload conjugate of claim 2 according to Formula IV wherein D is an auristatin.

11. The targeting unit-linker-payload conjugate of claim 2 according to Formula IV wherein D is is MMAU.

12. The targeting unit-linker-payload conjugate of claim 2 according to Formula IV wherein T is connected to X by a cysteine side chain via a thioether bond.

13. The targeting unit-linker-payload conjugate of claim 2 according to Formula IV wherein D is MMAU and T is trastuzumab.

14. The targeting unit-linker-payload conjugate of claim 2 according to Formula IV wherein T is connected to X by a cysteine side chain via a thioether bond and n is 5, 6, 7, or 8.

15. The targeting unit-linker-payload conjugate of claim 2 according to Formula IVb wherein D is an auristatin.

16. The targeting unit-linker-payload conjugate of claim 2 according to Formula IVb wherein D is MMAU.

17. The targeting unit-linker-payload conjugate of claim 2 according to Formula IVb wherein D is MMAU and T is trastuzumab.

18. The targeting unit-linker-payload conjugate of claim 2 according to Formula IV wherein D is an auristatin or MMAU.

19. A targeting unit-linker-payload conjugate of claim 2 that is:

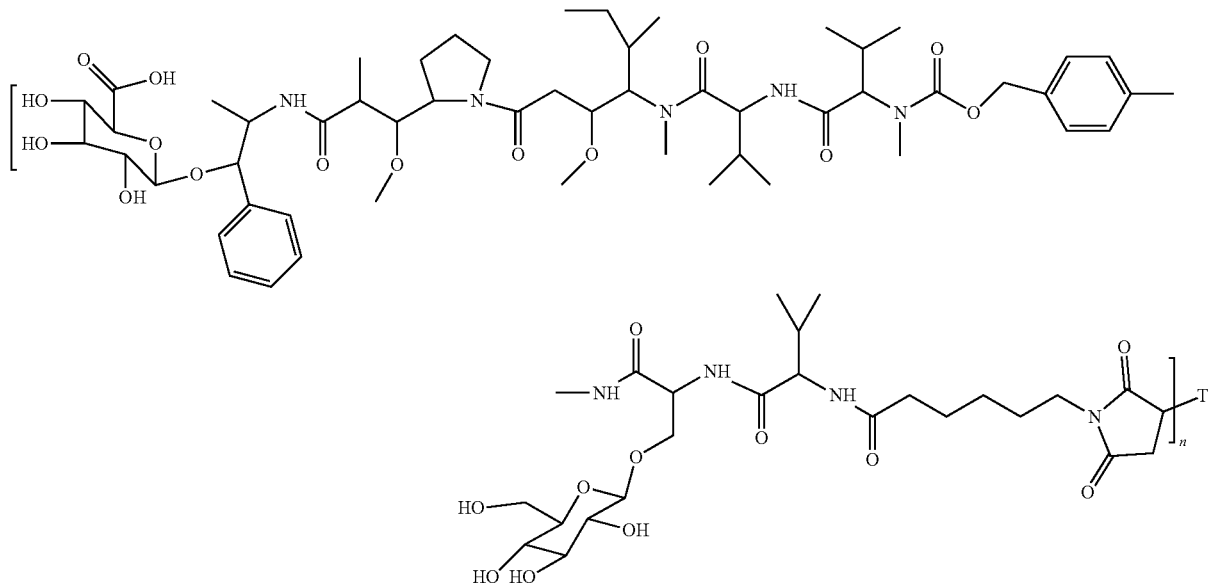

wherein T is an antibody connected by a cysteine side chain via a thioether bond.

20. The targeting unit-linker-payload conjugate of claim 19 wherein n is 5, 6, 7 or 8.

21. The targeting unit-linker-payload conjugate of claim 2 wherein T is trastuzumab.

22. The targeting unit-linker-payload conjugate of claim 2 wherein D is MMAU and T is trastuzumab.

23. The targeting unit-linker-payload conjugate of claim 2, wherein T is selected from the group consisting of bevacizumab, tositumomab, etanercept, trastuzumab, adalimumab, alemtuzumab, gemtuzumab ozogamicin, efalizumab, rituximab, infliximab, abciximab, basiliximab, palivizumab, omalizumab, daclizumab, cetuximab, panitumumab, epratuzumab, 2G12, lintuzumab, nimotuzumab and ibritumomab tiuxetan, an anti-EGFR1 antibody, an epidermal growth factor receptor 2 (HER2/neu) antibody, an anti-CD22 antibody, an anti-CD30 antibody, an anti-CD33 antibody, an anti-Lewis y antibody, and an anti-CD20 antibody.

24. The targeting unit-linker-payload conjugate of claim 2, wherein n is selected from the group consisting of 1, 2, 3, 4, 5, 6, 7, 8, 9, 10, 11, 12, 13, 14, 15, 16, 17, 18, 19, and 20.

25. The targeting unit-linker-payload conjugate of claim 24 wherein n is selected from the group consisting of 2, 4, 6, 7, and 8.

26. A method for preparing a targeting unit-linker-payload conjugate of claim 2, the method comprising conjugating a linker-payload conjugate of claim 1 to an antibody.

27. A pharmaceutical composition comprising the linker-payload conjugate of claim 1 and at least one pharmaceutically acceptable excipient.

28. A pharmaceutical composition comprising the targeting linker-payload conjugate of claim 2 and at least one pharmaceutically acceptable excipient.

* * * * *